US010428126B2

(12) United States Patent
Jiang et al.

(10) Patent No.: US 10,428,126 B2
(45) Date of Patent: Oct. 1, 2019

(54) DERMASEPTIN-TYPE AND PISCIDIN-TYPE ANTIMICROBIAL PEPTIDES

(71) Applicant: THE REGENTS OF THE UNIVERSITY OF COLORADO, a body corporate, Denver, CO (US)

(72) Inventors: Ziqing Jiang, Denver, CO (US); Robert S. Hodges, Aurora, CO (US); Lajos Gera, Centennial, CO (US); Colin T. Mant, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 16/241,583

(22) Filed: Jan. 7, 2019

(65) Prior Publication Data
US 2019/0202877 A1    Jul. 4, 2019

Related U.S. Application Data

(63) Continuation of application No. 15/114,037, filed as application No. PCT/US2015/012913 on Jan. 26, 2015, now Pat. No. 10,221,222.

(60) Provisional application No. 61/931,528, filed on Jan. 24, 2014.

(51) Int. Cl.
*C07K 14/00* (2006.01)
*C07K 14/46* (2006.01)
*A61K 38/00* (2006.01)

(52) U.S. Cl.
CPC .......... *C07K 14/463* (2013.01); *C07K 14/461* (2013.01); *A61K 38/00* (2013.01); *Y02A 50/471* (2018.01); *Y02A 50/473* (2018.01); *Y02A 50/481* (2018.01)

(58) Field of Classification Search
None
See application file for complete search history.

(56) References Cited

U.S. PATENT DOCUMENTS

| | | | |
|---|---|---|---|
| 1,022,122 | A1 | 3/2019 | Jiang et al. |
| 10,221,222 | B2 * | 3/2019 | Jiang ............... C07K 14/461 |
| 2003/0105281 | A1 | 6/2003 | Noga et al. |
| 2004/0132970 | A1 | 7/2004 | Loyter et al. |

FOREIGN PATENT DOCUMENTS

| | | | |
|---|---|---|---|
| KR | 2010/0065639 | * | 6/2010 |
| WO | WO 2013/039857 | | 3/2013 |

OTHER PUBLICATIONS

Bergaoui et al. "In vitro antiviral activity of dermaseptin S4 and derivatives from amphibian skin against herpes simplex virus type 2," Journal of Medical Virology, Feb. 2013, vol. 85, No. 2, pp. 272-281.

Campagna et al., "Structure and mechanism of action of the antimicrobial peptide piscidin," Biochemistry, 2007, vol. 46(7), pp. 1771-1778.

Chekmenev et al., "Investigating molecular recognition and biological function at interfaces using piscidins, antimicrobial peptides from fish," Biochimica et Biophysica Acta, 2006, vol. 1758, pp. 1359-1372.

Chen et al. "Rational Design of α-Helical Antimicrobial Peptides with Enhanced Activities and Specificity/Therapeutic Index," Journal of Biological Chemistry, Apr. 2005, vol. 280, No. 13, pp. 12316-12329.

Chen et al. "Comparison of Biophysical and Biologic Properties of α-Helical Enantiomeric Antimicrobial Peptides," Chemical Biology & Drug Design, Feb. 2006, vol. 67, No. 2, pp. 162-173.

Feder et al., "Structure-Activity Relationship Study of Antimicrobial Dermaseptin S4 Showing the Consequences of Peptide Oligomerization on Selective Cytotoxicity," The Journal of Biological Chemistry, 2000, vol. 275(6), pp. 4230-4238.

Jiang et al. "Rational Design of α-Helical Antimicrobial Peptides to Target Gram-negative Pathogens, Acinetobacter baumannii and Pseudomonas aeruginosa: Utilization of Charge, 'Specificity Determinants,' Total Hydrophobicity, Hydrophobe Type and Location as Design Parameters to Improve the Therapeutic Ratio," Chemical Biology & Drug Design, Apr. 2011, vol. 77, No. 4, pp. 225-240.

Jiang et al., "'Specificity Determinants' Improve Therapeutic Indices of Two Antimicrobial Peptides Piscidin 1 and Dermaseptin S4 Against the Gram-negative Pathogens Acinetobacter baumannii and Pseudomonas aeruginosa," Pharmaceuticals, 2014, vol. 7, 27 pages.

Kumar et al. "Piscidin-1-analogs with double L- and D-lysine residues exhibited different conformations in lipopolysaccharide but comparable anti-endotoxin activities," Scientific Reports, Jan. 2017, vol. 7, 39925.

Kumar et al. "Single Amino Acid Substitutions at Specific Positions of the Heptad Repeat Sequence of Piscidin-1 Yielded Novel Analogs That Show Low Cytotoxicity and In Vitro and In Vivo Antiendotoxin Activity," Antimicrobial Agents and Chemotherapy, Jun. 2016, vol. 60, No. 6, pp. 3687-3699.

(Continued)

Primary Examiner — Maury A Audet
(74) Attorney, Agent, or Firm — Sheridan Ross P.C.

(57) ABSTRACT

Antimicrobial agents, including antimicrobial peptides (AMPs) and uses thereof. Compositions and methods of using dermaseptin-type and piscidin-type antimicrobial peptides that demonstrate activity and improved therapeutic indices against microbial pathogens. The peptide compositions demonstrate the ability to not only maintain or improve antimicrobial activity against bacterial pathogens including Gram-negative microorganisms *Acinetobacter baumannii* and *Pseudomonas aeruginosa*, but also significantly decrease hemolytic activity against human red blood cells. Specificity determinants within the AMPS change selectivity from broad spectrum antimicrobial activity to AMPS with gram-negative selectivity.

13 Claims, 12 Drawing Sheets

Specification includes a Sequence Listing.

(56) References Cited

OTHER PUBLICATIONS

Lee et al., "Solution Structure and Cell Selectivity of Piscidin 1 and Its Analogues," Biochemistry, 2007, vol. 46(12), pp. 3653-3663.

Navon-Venezia et al. "Antibacterial Properties of Dermaseptin S4 Derivatives with In Vivo Activity," Antimicrobial Agents and Chemotherapy, Mar. 2002, vol. 46, No. 3, pp. 689-694.

Pinto et al. "Antimicrobial peptides isolated from Phyllomedusa nordestina (Amphibia) alter the permeability of plasma membrane of Leishmania and Trypanosoma cruzi," Experimental Parasitology, Dec. 2013, vol. 135, No. 4, pp. 655-660.

Salger et al. "A Diverse Family of Host-Defense Peptides (Piscidins) Exhibit Specialized Anti-Bacterial and Anti-Protozoal Activities in Fishes," PLOS One, Aug. 2016, vol. 11, No. 8, e0159423.

Yuan et al. "Molecular dynamics studies of the antimicrobial peptides piscidin 1 and its mutants with a DOPC lipid bilayer," Biopolymers, Dec. 2012, vol. 97, No. 12, pp. 998-1009.

Zairi et al., "In vitro spermicidal activity of peptides from amphibian skin: dermaseptin S4 and derivatives," Bioorg Med Chem, 2008, vol. 16(1), pp. 266-275.

International Search Report and Written Opinion for International (PCT) Patent Application No. PCT/US15/12913, dated Jul. 10, 2015, 12 pages.

International Preliminary Report on Patentability for International (PCT) Patent Application No. PCT/US15/12913, dated Aug. 4, 2016, 8 pages.

Extended Search Report for European Patent Application No. 15740068.0, dated Feb. 9, 2018 19 pages.

Official Action for U.S. Appl. No. 15/114,037, dated Jun. 30, 2017, 6 pages.

Official Action for U.S. Appl. No. 15/144,037, dated Aug. 24, 2017.

Notice of Allowance for U.S. Appl. No. 15/144,037, dated Jul. 6, 2018.

Notice of Allowance for U.S. Appl. No. 15/114,037, dated Oct. 4, 2018 12 pages.

Official Action for European Patent Application No. 15740068.0, dated Apr. 5, 2019 4 pages.

\* cited by examiner

DERMASEPTIN-TYPE AND PISCIDIN-TYPE ANTIMICROBIAL PEPTIDES

CROSS REFERENCE TO RELATED APPLICATION

This application is a continuation of U.S. patent application Ser. No. 15/114,037, filed Jul. 25, 2016, now U.S. Pat. No. 10,221,222, which is a U.S. national stage application under 35 U.S.C. 371 of PCT Application No. PCT/US2015/012913, having an international filing date of Jan. 26, 2015, which designated the United States, which PCT application claimed the benefit of U.S. Application Ser. No. 61/931,528, filed on Jan. 24, 2014, both of which are incorporated herein by reference in their entirety.

REFERENCE TO SEQUENCE LISTING

This application contains a Sequence Listing submitted as an electronic text file named "2848-173-PUS-1_Sequence_Listing_ST25.txt", having a size in bytes of 7000 bytes, and created on Jan. 7, 2019. The information contained in this electronic file is hereby incorporated by reference in its entirety pursuant to 37 CFR § 1.52(e)(5).

FIELD OF THE INVENTION

This application relates to the field of antimicrobial agents, including antimicrobial peptides (AMPs). The disclosure further relates to embodiments including compositions and methods comprising dermaseptin-type and piscidin-type antimicrobial peptides.

BACKGROUND

Emergence of antimicrobial resistance is becoming a very large public health threat and has been recognized by, amongst others, the World Health Organization, the U.S. Congress Office of Technology Assessment and the United Kingdom House of Lords. The urgency to develop new classes of antimicrobial agents particularly against Gram-negative pathogens *Acinetobacter baumannii* and *Pseudomonas aeruginosa*, was demonstrated by the dramatic increases in the incidence of antibiotic-resistant species in a recent study in Mexico. In one study, 550 clinical isolates of *A. baumannii* and 250 clinical isolates of *P. aeruginosa* were analyzed for the prevalence of multi-drug resistance, and 74% of *A. baumannii* and 34% of *P. aeruginosa* were multi-drug resistant.

Antimicrobial peptides (AMPs) are widely distributed in nature and represent a promising class of new antimicrobial agents. AMPs are rapidly bactericidal and generally have broad-spectrum activity. It is difficult for bacteria to develop resistance to AMPs because their mode of action involves nonspecific interactions with the cytoplasmic membrane. In addition, enantiomeric forms of AMPs with all-D-amino acids have shown equal activities to their all-L-enantiomers, suggesting that the antimicrobial mechanism of such peptides does not involve a stereoselective interaction with a chiral enzyme or lipid or protein receptor. In addition, all D-peptides are resistant to proteolytic enzyme degradation, which enhances their potential as therapeutic agents. However, it is widely believed that native AMPs lack specificity and might be too toxic (including due to the ability to lyse mammalian cells, normally expressed as hemolytic activity against human red blood cells) to be used for systemic treatment.

The Dermaseptins are a family of linear peptides, initially isolated in 1991 from the skin of various tree-dwelling, South American frogs of the *Phyllomedusa* species. These amphipathic α-helical cationic antimicrobial family of peptides are structurally and functionally related. They exhibit rapid cytolytic activity against a variety of microorganisms including viruses, bacteria, protozoa, yeast and filamentous fungi. Unlike other Dermaseptin members, Dermaseptin S4, a 28-residue AMP, lyses erythrocytes at micromolar concentrations. (The Dermaseptin S4 was originally identified as a 28-mer peptide, but a deletion of a single residue in the sequence by the inventors produced an active 27-mer. For accuracy, the two peptides are referred to herein as "Dermaseptin S4, 27-mer", and "Dermaseptin S4, 28-mer." The sequences of these peptides are shown in Table 5 and additional data regarding the two forms is shown in FIG. 3.) The $HC_{50}$, the peptide concentration that causes 50% lysis of human red blood cells, was approximately 1.4 µM using a three hour incubation time at 37° C. Very rapid kinetics (within seconds) for the lysis of human red blood cells can be observed under a microscope. This hemolytic activity of these peptides is a significant disadvantage for the therapeutic use of these peptides.

The Piscidin family comprises the most common group of AMPs in teleost fish. Piscidin 1 was first isolated in 2001 from hybrid striped bass (*Morone saxatilis* male×*Morone chrysops* female), where it is produced in mast cells (immune cells of uncertain function present in all vertebrates), skin, gill and gastrointestinal tract. Piscidin 1 is a 22-residue amphipathic α-helical AMP rich in histidines and phenylalanines. Piscidin 1 has the highest biological activity among the family with broad-spectrum activity against antibiotic-resistant bacteria, filamentous fungi, yeasts, and viruses. This peptide, however, is not selective for bacterial versus mammalian cells, and caused hemolysis of human red blood cells with a $HC_{50}$ of 11~20 µM within one hour at 37° C. Thus, both AMPs from different natural sources suffer the dose or drug-limiting toxicity of hemolytic activity.

Thus, a new class of antimicrobial agents with lower rates of resistance and different microbial targets is urgently needed because of the rapidly increasing resistance to classical antibiotics. Amphipathic cationic α-helical antimicrobial peptides (AMPs) represent such a class of compounds, but the toxicity of these compounds to mammalian cells must be overcome.

SUMMARY

The invention provides antimicrobial agents comprising peptides and peptide-containing compositions. In related embodiments, the invention provides methods of inhibiting microorganisms. In certain embodiments, the invention provides methods of treating a subject by administering an antimicrobial peptide (AMP) or composition containing one or more AMPs described herein. In embodiments, compositions and methods of AMPs are described which demonstrate activity and improved therapeutic indices against bacterial pathogens. In embodiments, peptide compositions demonstrate the ability to not only maintain or improve antimicrobial activity against bacterial pathogens including Gram-negative microorganisms *Acinetobacter baumannii* and *Pseudomonas aeruginosa*, but also significantly decrease the hemolytic activity against human red blood cells. Thus, improved therapeutic indices are achieved by AMPs disclosed herein.

To overcome the significant mammalian toxicity of most of the known AMPs, the inventors developed the design concept of the "specificity determinant" which, in embodiments described herein, refers to substituting positively charged residue(s) in the non-polar face of amphipathic α-helical or cyclic β-sheet within antimicrobial peptides to create selectivity between eukaryotic and prokaryotic membranes; that is, antimicrobial activity is maintained and hemolytic activity or cell toxicity to mammalian cells is decreased or eliminated.

The inventors selected Piscidin 1 and Dermaseptin S4 as examples of native AMPs to substitute one or two amino acid(s) to lysine(s) at different positions in their non-polar faces to investigate and develop the application of the "specificity determinant" design concept to enhance or maintain antimicrobial activity and significantly improve the therapeutic index.

This disclosure provides antimicrobial agents comprising peptide compositions, as well as methods of inhibiting microorganisms. In an embodiment, this disclosure provides a method of treating a subject by administering a composition as described herein. In embodiments, antimicrobial peptides (AMPs) are described which demonstrate activity and improved therapeutic indices against bacterial pathogens. The peptides may demonstrate the ability to not only maintain or improve antimicrobial activity against bacterial pathogens, including Gram-negative microorganisms *Acinetobacter baumannii* and *Pseudomonas aeruginosa*, but also significantly decrease the hemolytic activity against human red blood cells. Thus, improved therapeutic indices are achieved by the disclosed AMPs.

In an aspect, this disclosure provides an isolated peptide comprising the amino acid sequence of D-Dermaseptin S4 L7K/A14K (ALWMTLKKKVLKAKAKALNAVLVGANA, SEQ ID NO:9) or a variant or derivative thereof, and wherein the peptide does not have the sequence of D-Dermaseptin S4 (27-mer) (ALWMTLLKKVLKAAAKALNAVLVGANA; SEQ ID NO:6).

In related aspects, this disclosure provides a variant of the D-Dermaseptin S4 L7K/A14K peptide, wherein the variant has one, two, or three amino acid modifications shown in the peptides of Tables 1 and 5.

In another aspect, this disclosure provides a peptide comprising the sequences of D-Dermaseptin S4 L7K/A14K. In another aspect, this disclosure provides a peptide consisting of the sequences of D-Dermaseptin S4 L7K/A14K.

In these embodiments, the peptides may have one or more improved biological properties relative to D-Dermaseptin S4 (27-mer), wherein said one or more properties are selected from the group consisting of antimicrobial activity, hemolytic activity, stability, and therapeutic index for a microorganism.

Another aspect of this disclosure provides a pharmaceutical composition comprising at least one of the antimicrobial peptides of this disclosure. In a specific embodiment, the pharmaceutical composition comprises a peptide consisting of the sequence of D-Dermaseptin S4 L7K/A14K (SEQ ID NO:9).

Another embodiment provides a method of preventing or treating an infection in a subject, wherein the method comprises the step of administering a therapeutically effective amount of a composition to the subject, wherein the composition comprises at least one antimicrobial peptide of embodiment 1 and a pharmaceutically acceptable carrier. In certain embodiments, the microorganism is selected from the group consisting of gram-positive bacteria and gram-negative bacteria.

Another embodiment provides a method of inhibiting a microorganism, the method comprising contacting the microorganism with a composition comprising at least one antimicrobial peptide of this disclosure.

Another embodiment provides an isolated peptide comprising the amino acid sequence of at least the first 16 residues of D-Dermaseptin S4 L7K/A14K (SEQ ID NO:9) or a variant or derivative thereof, and wherein the peptide does not have the sequence of D-Dermaseptin S4 (SEQ ID NO:6).

Another embodiment provides an isolated peptide comprising the amino acid sequence of the peptide selected from the group consisting of any of the antimicrobial peptides of this disclosure, including a peptide of Tables 1 or 5, and a derivative or variant thereof, that maintains substantially similar antimicrobial activity compared to the D-Dermaseptin S4 L7K/A14K peptide.

One aspect of this disclosure provides an antimicrobial peptide (AMP) comprising an amino acid sequence having at least 85%, or at least 90% or at least 95% homology with a peptide selected from the group consisting of:

```
                                           (SEQ ID NO: 2)
NH2-FFHHIFRPIVHVGKTIHRLVTG-amide;

(SEQ ID NO: 3)
NH2-FFHHIFRGKVHVGKTIHRLVTG-amide (SEQ ID NO: 4)
NH2-FFHHIFRGIVHKGKTIHRLVTG-amide (SEQ ID NO: 5)
NH2-FFHHIFRGIVHVKKTIHRLVTG-amide (SEQ ID NO: 7)
NH2-ALWMTLKKKVLKAAAKALNAVLVGANA-amide (SEQ ID NO: 8)
NH2-ALWMTLLKKVLKAKAKALNAVLVGANA-amide (SEQ ID NO: 9)
NH2-ALWMTLKKKVLKAKAKALNAVLVGANA-amide (SEQ ID NO: 12)
NH2-ALWMTLKKKVLKAKAKAALNVALVGANA-amide (SEQ ID NO: 13)
NH2-ALWMTLKKKVLKAKAK-amide (SEQ ID NO: 14)
NH2-ALWMTKLKKVLKAKAKALNAVLVGANA-amide (SEQ ID NO: 15)
NH2-ALWMTLKKKVLKAKAKALNAVLSGANA-amide (SEQ ID NO: 16)
NH2-ALWMTLKKKVLKAKAKALNAVLKGANA-amide (SEQ ID NO: 17)
NH2-ALWMTLKKKVLKAKAKALNAVLAGVNA-amide (SEQ ID NO: 18)
NH2-ALWMTLKKKVLKAKAKLLNAVLVGANA-amide (SEQ ID NO  19)
NH2-ALWMTLKKKVLKAKAKALNAVLVGANA-amide,
and (SEQ ID NO: 20)
NH2-ALWMTLKKKVLKAKAKLLNAVLVGLNA-amide,
``` or functional analogues, derivatives or fragments thereof, or a pharmaceutically-acceptable salt thereof.

In certain embodiments, the AMP comprises the sequence of any one of SEQ ID NOs.: 2-5, 7-9, and 12-20. In related embodiments, the AMP consists of the sequence of any one of SEQ ID NOs.: 2-5, 7-9, and 12-20. In specific embodiments, the AMP comprises the sequence of any one of SEQ ID NOs.:2-5. In specific embodiments, the AMP comprises the sequence of any one of SEQ ID NOs.:7-9. In specific embodiments, the AMP comprises the sequence of any one of SEQ ID NOs.:12-20. In a preferred embodiment, the amino acid sequence of the AMP comprises the sequence of SEQ ID NO:9. In a related embodiment, the amino acid sequence of the AMP consists of the sequence of SEQ ID NO:9. In these embodiments, the AMP inhibits propagation of a prokaryote. In certain embodiments, the prokaryote is a Gram negative bacterium, which may include at least one of *A. baumannii* and *P. aeruginosa*. In other embodiments, the prokaryote is a Gram-positive bacterium which may include methicillin-resistant *Staphylococcus aureus* (MRSA).

In certain embodiments, the AMP exhibits at least a 3-fold increased selectivity for Gram negative bacteria over Gram-positive bacteria compared to the selectivity of SEQ ID NO:1.

In related embodiments, the AMP exhibits at least a 50-fold increased selectivity for Gram negative bacteria over Gram-positive bacteria compared to the selectivity of SEQ ID NO. 1.

In certain embodiments, the AMP exhibits at least a 3-fold increased selectivity for Gram negative bacteria over Gram-positive bacteria compared to the selectivity of SEQ ID NO:6.

In related embodiments, the AMP exhibits at least a 100-fold increased selectivity for Gram negative bacteria over Gram-positive bacteria compared to the selectivity of SEQ ID NO:6.

In certain embodiments the AMP exhibits at least a 3-fold increased selectivity for prokaryotic cells over eukaryotic cells compared to the selectivity of SEQ ID NO: 1. In related embodiments, the AMP exhibits at least a 30-fold increased selectivity for prokaryotic cells over eukaryotic cells compared to the selectivity of SEQ ID NO:1. In certain embodiments, the AMP exhibits at least a 10-fold increased selectivity for prokaryotic cells over eukaryotic cells compared to the selectivity of SEQ ID NO:6. In related embodiments, the AMP exhibits at least a 400-fold increased selectivity for prokaryotic cells over eukaryotic cells compared to the selectivity of SEQ ID NO:6. In related embodiments, the AMP exhibits at least a 700-fold increased selectivity for prokaryotic cells over eukaryotic cells compared to the selectivity of SEQ ID NO:6.

In certain embodiments, the AMP exhibits at least a 15-fold decreased hemolysis of human red blood cells compared to hemolysis exhibited by SEQ ID NO: 1. In related embodiments, the AMP exhibits at least a 50-fold decreased hemolysis of human red blood cells compared to hemolysis exhibited by SEQ ID NO:1. In certain embodiments, the AMP exhibits at least a 10-fold decreased hemolysis of human red blood cells compared to hemolysis exhibited by SEQ ID NO:6. In related embodiments, the AMP exhibits at least a 400-fold decreased hemolysis of human red blood cells compared to hemolysis exhibited by SEQ ID NO:6.

In these embodiments, the antibiotic resistant prokaryote may be a gram-negative resistant *Acinetobacter baumannii* or *Pseudomonas aeruginosa* pathogen and an antibiotic sensitive prokaryote may be an *Acinetobacter baumannii* or *Pseudomonas aeruginosa* sensitive pathogen. Alternatively or additionally, the antibiotic resistant prokaryote may be a colistin (polymyxin E) resistant gram-negative pathogen or a colistin sensitive gram-negative pathogen.

Another aspect of this disclosure provides a pharmaceutical composition comprising at least one AMP of this disclosure and a pharmaceutically acceptable carrier. In one embodiment, the pharmaceutical composition is a monophasic pharmaceutical composition suitable for parenteral or oral administration consisting essentially of a therapeutically-effective amount of at least one AMP of this disclosure, and a pharmaceutically acceptable carrier.

Another aspect of this disclosure provides methods of preventing or treating a microbial infection comprising administering to a subject in need thereof a therapeutically effective amount of at least one AMP of this disclosure, or a pharmaceutical composition comprising the same.

In these methods, the microbial infection may be the result of an infecting bacteria, fungi, virus, or protozoa. In certain embodiments, the microbial infection is a bacterial infection. In specific embodiments, the bacterial infection is a Gram negative bacterial infection. In related embodiments, the bacterial infection is an antibiotic resistant bacterial infection. In certain embodiments, the infecting microorganism is at least one of *Escherichia coli, Pseudomonas aeruginosa, Salmonella* spp., *Hemophilus influenza, Neisseria* spp., *Vibrio cholerae, Vibrio parahaemolyticus* and *Helicobacter pylori*. In specific embodiments, the infecting microorganism is the yeast *Candida albicans*. In certain embodiments, the infecting microorganism is at least one of measles virus, herpes simplex virus (HSV-1 and -2), herpes family members (HIV, hepatitis C, vesicular, stomatitis virus (VSV), visna virus, and cytomegalovirus (CMV). In another embodiment, the infecting microorganism is at least one of *Giardia, Acinetobacter baumannii* and *Pseudomonas aeruginosa*. In a specific embodiment, the infecting microorganism is multi-drug resistant *Pseudomonas aeruginosa* or *Acinetobacter baumannii* bacteria.

In these methods, the administration of the peptide or pharmaceutical composition may be made by an administration route selected from oral, topical, intravenous, intraperitoneal, intramuscular, intradermal, intrasternal, intraarticular injection, or infusion. In certain embodiments, the peptide or pharmaceutical composition is administered in conjunction with one or more additional antimicrobial agents.

Another embodiment is a method of preventing a microbial infection in an individual at risk of developing an infection comprising administering an effective amount of at least one AMP of this disclosure or a pharmaceutical composition comprising the same to an individual in need thereof. In certain embodiments, the individual is a surgical patient. In related embodiments, the individual is a hospitalized patient.

A method of combating a bacterial infection in a patient, comprising applying at least one AMP of this disclosure or a pharmaceutical composition comprising the same to a body surface of the patient. In a specific embodiment, the body surface is a wound. In a specific embodiment, the composition is applied following an operation or surgery.

Another embodiment provides at least one AMP of this disclosure or a pharmaceutical composition comprising the same for use in the treatment of a microbial infection. A related embodiment provides the use of at least one peptide of this disclosure or a pharmaceutical composition comprising the same in the manufacture of a medicament for the prevention or treatment of a microbial infection.

BRIEF DESCRIPTION OF THE DRAWINGS

FIG. 4A shows the CD spectra of D-Pisicidin 1 analogs in aqueous benign buffer (100 mM KCl, 50 mM NaH$_2$PO$_4$/Na$_2$HPO$_4$ at pH 7.0), 5° C. (closed symbols) and in the presence of buffer-trifluoroethand (TFE) (1:1, v/v) (open symbols). FIG. 4B shows the CD spectra of D-Dermaseptin S4 analogs in aqueous benign buffer (100 mM KCl, 50 mM NaH$_2$PO$_4$/Na$_2$HPO$_4$ at pH 7.0), 5° C., and FIG. 4C shows D-Dermaseptin S4 analogs in the presence of buffer-trifluoroethanol (TFE) (1:1, v/v).

FIG. 9A shows a helical wheel configuration with non-polar and polar faces indicated as an open arc (double lines) and solid arc (single thick line), respectively. FIG. 9B shows the helical net representations of the polar and non-polar faces of the peptide. The one-letter code is used for amino acid residues. 'D' denotes that all residues in the peptides are in the D conformation. Positively charged residues (Lys) are shaded black, large hydrophobes (Val, Leu, Met and Trp) have hatched shading. The "specificity determinants" are denoted by black triangle(s). In the helical net representations of FIG. 9B, the residues on the polar face are boxed and the residues on the non-polar face are circled. The i→i+3 and i→i+4 potential hydrophobic interactions along the helix are shown as solid black bars. The i→i+3 and i→i+4 potential electrostatic repulsions between positively charged residues along the helix are shown as dotted bars.

DETAILED DESCRIPTION

Figure 1:
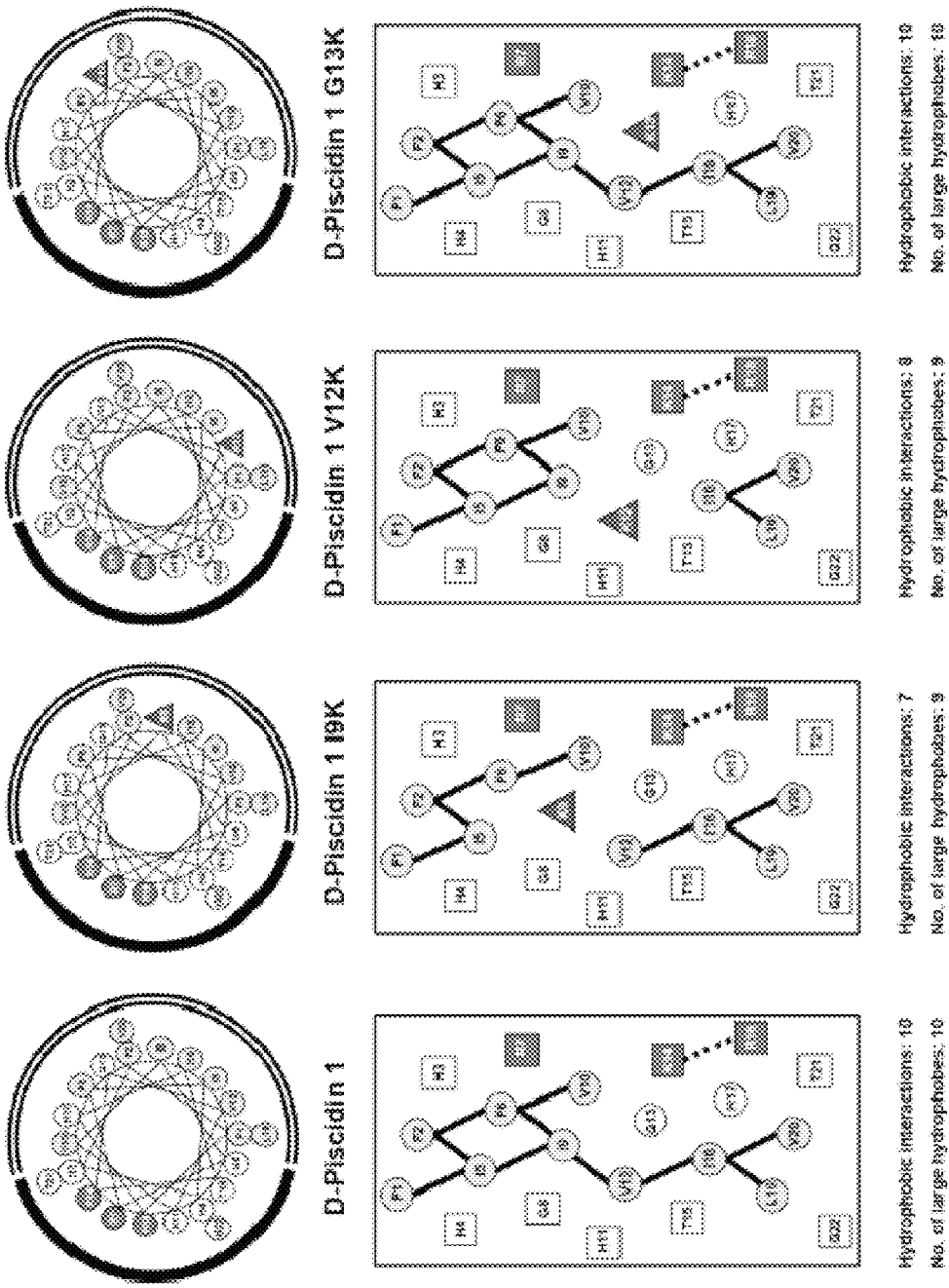
FIG. 1 shows helical wheel (upper panel) and helical net (lower panel) representations of D-Piscidin 1 and related peptide analogs listed in Table 1. The one-letter code is used for amino acid residues. 'D' denotes that all residues in the peptides are in the D-conformation. Positively charged residues (Lys and Arg) are darkly shaded on the left side of the helical wheel and the right side of the helical net. Large hydrophobes (Val, Ile, Leu and Phe) are lightly shaded on the right side of the helical wheel and the left side of the helical net. The "specificity determinant" amino acid change is denoted by shaded triangles in the three D-Pisicidin 1 analogs of the invention. In the helical wheel, the non-polar face is indicated as an open arc (double lines) and the polar face is shown as a solid arc (single thick line). In the helical net, the residues on the polar face are boxed and the residues on the non-polar face are circled. The i→i+3 and i→i+4 potential hydrophobic interactions along the helix are shown as black bars. The i→i+3 and i→i+4 potential electrostatic repulsions between positively charged residues along the helix are shown as dotted bars.

In general the terms and phrases used herein have their art-recognized meaning, which can be found by reference to standard texts, journal references and contexts known to those skilled in the art.

As used herein, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "containing" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the pertinent art.

Whenever a range of values is given in the specification, for example, a temperature range, a time range, or a composition or concentration range, all intermediate ranges and subranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be optionally replaced with either of the other two terms, thus describing alternative aspects of the scope of the subject matter. The invention illustratively described herein suitably may be practiced in the absence of any element or elements, limitation or limitations which is not specifically disclosed herein.

The following definitions are provided to clarify use of these terms in the context of embodiments of the invention.

When used herein, the term "amino acid" is intended to refer to any natural or unnatural amino acid, whether made naturally or synthetically, including any such in L- or D-configuration. The term can also encompass amino acid analog compounds used in peptidomimetics or in peptoids. The term can include a modified or unusual amino acid or a synthetic derivative of an amino acid, e.g. diamino butyric acid and diamino propionic acid and the like. In embodiments, of antimicrobial peptides comprise amino acids linked together by peptide bonds. The peptides are in general in alpha helical conformation under hydrophobic conditions. Sequences are conventionally given from the amino terminus to the carboxyl terminus. Unless otherwise noted, the amino acids are L-amino acids. When all the amino acids are of L-configuration, the peptide is said to be an L-enantiomer. When all the amino acids are of D-configuration, the peptide is said to be a D-enantiomer.

The term "hemolytic concentration—50 or $HC_{50}$" refers to the peptide concentration that causes 50% hemolysis of erythrocytes after 18 h. $HC_{50}$ was determined from a plot of percent lysis versus peptide concentration (μM). For comparison, the inventors also determined the hemolytic activity after 1 hour at 37° C. Hemolysis can be determined with red blood cells (RBC) from various species including human red blood cells (hRBC).

The term "therapeutic index" (TI) is the ratio of $HC_{50}$ over minimal inhibitory concentration (MIC) of an antimicrobial agent. Larger values generally indicate greater antimicrobial specificity.

The term "stability" can refer to an ability to resist degradation, to persist in a given environment, and/or to maintain a particular structure. For example, a peptide property of stability can indicate resistance to proteolytic degradation and to maintain an alpha-helical structural conformation.

The following abbreviations are used herein: A, Ala, Alanine; M, Met, Methionine; C, Cys, Cysteine, D, Asp, Aspartic Acid, E, Glu, Glutamic Acid; F, Phe, Phenylalanine; G, Gly, Glycine; H, His, Histidine; I, Ile, Isoleucine; K, Lys, Lysine; L, Leu, Leucine; N, Asn, Asparagine, P, Pro, Proline; Q, Glu, Glutamine; R, Arg, Arginine; S, Ser, Serine; T, Thr, Threonine; V, Val, Valine; W, Trp, Tryptophan; Y, Tyr, Tyrosine; RP-HPLC, reversed-phase high performance liquid chromatography, MIC, minimal inhibitory concentration; $HC_{50}$ hemolytic concentration—50; CD, circular dichroism spectroscopy; TFE, 2,2,2-trifluoroethanol; TFA, trifluoroacetic acid; RBC, red blood cells; hRBC, human red blood cells.

The term "antimicrobial activity" refers to the ability of a peptide embodiment to modify a function or metabolic process of a target microorganism, for example so as to at least partially affect replication, vegetative growth, toxin production, survival, viability in a quiescent state, or other attribute. In an embodiment, the term relates to inhibition of growth of a microorganism. In a particular embodiment, antimicrobial activity relates to the ability of a peptide to kill at least one bacterial species. In a particular embodiment, the bacterial species is selected from the group consisting of gram-positive and gram-negative bacteria. In an embodiment, the term can be manifested as microbicidal or microbistatic inhibition of microbial growth.

The phrase "improved biological property" is meant to indicate that a test peptide exhibits less hemolytic activity and/or better antimicrobial activity, or better antimicrobial activity and/or less hemolytic activity, compared to the control peptide (e.g., D-Piscidin 1 or D-Dermaseptin S4), when tested by the protocols described herein or by any other art-known standard protocols. In general, the improved biological property of the peptide is reflected in the therapeutic index (TI) value which is better than that of the control peptide.

The term "microorganism" herein refers broadly to bacteria, fungi, viruses, and protozoa. In particular, the term is applicable for a microorganism having a cellular or structural component of a lipid bilayer membrane. In specific embodiments, the membrane is a cytoplasmic membrane. Pathogenic bacteria, fungi, viruses, and protozoa as known in the art are generally encompassed. Bacteria can include gram-negative and gram-positive bacteria in addition to organisms classified in orders of the class Mollicutes and the like, such as species of the *Mycoplasma* and *Acholeplasma* genera. Specific examples of potentially sensitive gram-negative bacteria include, but are not limited to, *Escherichia coli, Pseudomonas aeruginosa. Salmonella* spp., *Hemophilus influenza, Neisseria* spp., *Vibrio cholerae, Vibrio parahaemolyticus* and *Helicobacter pylori*. Examples of potentially sensitive gram-positive bacteria include, but are not limited to, *Staphylococcus aureus, Staphylococcus epidermidis, Streptococcus agalactiae,* Group A *Streptococcus, Streptococcus pyogenes, Enterococcus faecalis,* Group B Gram-positive *Streptococcus, Corynebacterium xerosis,* and *Listeria monocytogenes*. Examples of potentially sensitive fungi include yeasts such as *Candida albicans*. Examples of potentially sensitive viruses include measles virus, herpes simplex virus (HSV-1 and -2), herpes family members (HIV, hepatitis C, vesicular, stomatitis virus (VSV), visna virus, and cytomegalovirus (CMV). Examples of potentially sensitive protozoa include *Giardia*.

"Therapeutically effective amount" as used herein, refers to an amount of formulation, composition, or reagent in a pharmaceutically acceptable carrier or a physiologically acceptable salt of an active compound that is of sufficient quantity to ameliorate the undesirable state of the patient, animal, material, or object so treated. "Ameliorate" refers to a lessening of the detrimental effect of the disease state or disorder, or reduction in contamination, in the receiver of the treatment.

"Pharmaceutical agent or drug" as used herein, refers to a chemical compound or composition capable of inducing a desired therapeutic or prophylactic effect when properly administered to a subject.

"Pharmaceutically acceptable carrier" as used herein, refers to conventional pharmaceutical carriers useful in the methods disclosed herein. Remington's Pharmaceutical Sciences, by E. W. Martin, Mack Publishing Co., Easton, Pa., 15th Edition (1975), describes compositions and formulations suitable for pharmaceutical delivery of TCR peptides and additional pharmaceutical agents. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween, sodium acetate or sorbitan monolaurate.

Antimicrobial peptides (AMPs) of the invention have antimicrobial activity by themselves or when covalently conjugated or otherwise coupled or associated with another molecule, e.g., polyethylene glycol or a carrier protein such as bovine serum albumin, so long as the peptides are positioned such that they can come into contact with a cell or unit of the target microorganism. These peptides may be modified by methods known in the art provided that the antimicrobial activity is not destroyed or substantially compromised.

In embodiments of the invention, peptide compositions may be isolated or purified. In embodiments, a peptide is synthetic and can be produced by peptide synthesis techniques or by recombinant expression technology as understood in the art. As used herein, the term "purified" can be understood in embodiments to refer to a state of enrichment or selective enrichment of a particular component relative to an earlier state of crudeness or constituency of another component. In embodiments, the term can be considered to correspond to a material that is at least partially purified as opposed to a state of absolute purity. For example in a particular embodiment, a peptide composition can be considered purified even if the composition does not reach a level of one hundred percent purity with respect to other components in the composition.

As used herein, the term "specificity determinant(s)" refers to certain amino acid residues in an AMP of the invention. In particular embodiments, the term refers to positively charged residue(s) in the non-polar face of AMPs that could decrease hemolytic activity/toxicity but increase or maintain the same level of antimicrobial activity, thus increasing the therapeutic index of the AMP.

Exemplary antimicrobial pedptides of the invention are listed in Table 1. Additional antimicrobial pedptides of the invention are listed in Table 5.

TABLE 1

Piscidin-type and Dermaseptin-type peptides

| Peptide Name[a] | Length | Sequence[b] | SEQ ID NO. | MW |
|---|---|---|---|---|
| D-Piscidin 1 | 22 | NH$_2$-FFHHIFRGIVHVGKTIHRLVTG-amide | 1 | 2571 |
| D-Piscidin 1 G8P[c] | 22 | NH$_2$-FFHHIFRPIVHVGKTIHRLVTG-amide | 2 | 2611 |
| D-Piscidin 1 I9K | 22 | NH$_2$-FFHHIFRGKVHVGKTIHRLVTG-amide | 3 | 2586 |
| D-Piscidin 1 V12K | 22 | NH$_2$-FFHHIFRGIVHKGKTIHRLVTG-amide | 4 | 2600 |
| D-Piscidin 1 G13K | 22 | NH$_2$-FFHHIFRGIVHVKKTIHRLVTG-amide | 5 | 2642 |
| D-Dermaseptin S4 | 27 | NH$_2$-ALWMTLLKKVLKAAAKALNAVLVGANA-amide | 6 | 2778 |
| D-Dermaseptin S4 L7K | 27 | NH$_2$-ALWMTLKKKVLKAAAKALNAVLVGANA-amide | 7 | 2794 |
| D-Dermaseptin S4 A14K | 27 | NH$_2$-ALWMTLLKKVLKAKAKALNAVLVGANA-amide | 8 | 2837 |
| D-Dermaseptin S4 L7K, A14K | 27 | NH$_2$-ALWMTLKKKVLKAKAKALNAVLVGANA-amide | 9 | 2851 |
| Control C[d] | 18 | Ac-ELEKGGLEGEKGGKELEK-amide | 10 | — |

[a]The D- denotes that all amino acid residues in each peptide are in the D conformation.
[b]Peptide sequences are shown using the one-letter code for amino acid residues; Ac denotes N$^\alpha$-acetyl and amide denotes C$^\alpha$-amide. The "specificity determinant(s)", Lys residues incorporated in the non-polar face are bolded.
[c]The L-Piscidin 1 G8P was previously reported as a selective peptide.
[d]This peptide is a random coil peptide in the all L-conformation used as a control for reversed-phase chromatography temperature profiling to examine peptide self-association.

Compositions of the Invention

When employed as pharmaceuticals, especially as antimicrobial agents administered to mammals, the AMPs of the invention are administered in the form of pharmaceutical compositions. These compounds can be administered by a variety of routes including oral, rectal, transdermal, subcutaneous, intravenous, intramuscular, and intranasal. Such pharmaceutical compositions are prepared in a manner well known in the pharmaceutical art and comprise at least one AMP of the invention.

The pharmaceutical compositions of the present invention contain, as the active ingredient, one or more of the AMPs of the invention, associated with pharmaceutically acceptable formulations. In making the compositions of this invention, the active ingredient is usually mixed with an excipient, diluted by an excipient or enclosed within a carrier which can be in the form of a capsule, sachet, paper or other container. An excipient is usually an inert substance that forms a vehicle for a drug. When the excipient serves as a diluent, it can be a solid, semi-solid, or liquid material, which acts as a vehicle, carrier or medium for the active ingredient. Thus, the compositions can be in the form of solutions, syrups, aerosols (as a solid or in a liquid medium), ointments containing, for example, up to 30% by weight of the active compound, soft and hard gelatin capsules, suppositories, sterile injectable solutions, and sterile packaged powders.

In preparing a formulation, it may be necessary to mill active compounds of the invention to provide the appropriate particle size prior to combining with the other ingredients. If the antimicrobial peptide is substantially insoluble, it ordinarily is milled to a particle size of less than 200 mesh. If the compound(s) is substantially w ater soluble, the particle size is normally adjusted by milling to provide a substantially uniform distribution in the formulation, e g. about 40 mesh.

Some examples of suitable excipients include lactose, dextrose, sucrose, sorbitol, mannitol, starches, gum acacia, gum Arabic, calcium phosphate, alginates, tragacanth, gelatin, calcium silicate, microcrystalline cellulose, polyvinylpyrrolidone, cellulose, sterile water, syrup, and methylcellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxy propylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, w ater or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxy ethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, poly ethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of compounds of this invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required.

The ointments, pastes, creams and gels may contain, in addition to an active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active ingredient, excipients such as lactose, talc, silicic acid, aluminum hydroxide, calcium silicates and poly amide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical formulations include those suitable for administration by inhalation or insufflation or for nasal or intraocular administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Typical of atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Liquid spray s are conveniently delivered from pressurized packs. Drops can be delivered by means of a simple eye dropper-capped bottle or by means of a plastic bottle adapted to deliver liquid contents dropwise by means of a specially shaped closure.

Pharmaceutical compositions of this invention suitable for parenteral administrations comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Suitable alkalinizing agents include alkali metal salts and alkaline earth metal salts. The alkali metal salts include sodium carbonate, sodium hydroxide, sodium silicate, disodium hydrogen orthophosphate, sodium aluminate, and other suitable alkali metal salts or mixtures thereof. Suitable alkaline metal salts include calcium carbonate, calcium hydroxide, magnesium carbonate, magnesium hydroxide, magnesium silicate, magnesium aluminate, aluminum magnesium hydroxide or mixture thereof. More particularly, calcium carbonate, potassium bicarbonate, calcium hydroxide, and/or sodium carbonate may be used as alkalinizing agents to obtain a formulation pH within the desired pH range of pH 8 to pH 13. The concentration of the alkalinizing agent is selected to obtain the desired pH, varying from about 0.1% to about 30%, by weight, and more preferably from about 12.5% to about 30%, by weight, of the total weight of the dosage formulation.

Suitable antioxidants may be selected from amongst one or more pharmaceutically acceptable antioxidants known in the art. Examples of pharmaceutically acceptable antioxidants include butylated hydroxyanisole (BHA), sodium ascorbate, butylated hydroxytoluene (BHT), sodium sulfite, citric acid, malic acid and ascorbic acid. The antioxidants may be present in the dosage formulations of the present invention at a concentration between about 0.001% to about 5%, by weight, of the dosage formulation.

Suitable chelating agents may be selected from amongst one or more chelating agents known in the art. Examples of suitable chelating agents include disodium edetate (EDTA), edetic acid, citric acid and combinations thereof. The chelating agents may be present in a concentration between about 0.001% and about 5%, by weight, of the dosage formulation.

Methods for Preventing and Treating Microbial Infection

Another aspect of the invention provides methods for preventing and treating a microbial infection. These methods include administering to a subject in need thereof a therapeutically effective amount of a peptide or composition of the invention that kills or inhibits the growth of infectious microbes, thereby inhibiting or treating the microbial infections.

In certain embodiments, the infectious microbes include at least one of bacteria, fungi, viruses, and protozoa. In certain embodiments, the infecting microorganism includes gram-negative and/or gram-positive bacteria in addition to organisms classified in orders of the class Mollicutes and the like, such as species of the *Mycoplasma* and *Acholeplasma* genera. In specific embodiments, the infecting microorganism is a gram-negative bacteria, which may include, but is not limited to, *Escherichia coli, Pseudomonas aeruginosa. Salmonella* spp., *Hemophilus influenza, Neisseria* spp., *Vibrio cholerae, Vibrio parahaemolyticus* and *Helicobacter pylori*.

In specific embodiments, the infecting microorganism is a gram-positive bacteria, including, but are not limited to, *Staphylococcus aureus, Staphylococcus epidermidis, Streptococcus agalactiae*, Group A *Streptococcus. Streptococcus pyogenes, Enterococcus faecalis*. Group B Gram-positive *Streptococcus, Corynebacterium xerosis*, and *Listeria monocytogenes*.

In specific embodiments, the infecting microorganism is a fungi, including, but not limited to, yeasts such as *Candida albicans*.

In specific embodiments, the infecting microorganism is a virus, including, but not limited to, measles virus, herpes simplex virus (HSV-1 and -2), herpes family members (HIV, hepatitis C, vesicular, stomatitis virus (VSV), visna virus, and cytomegalovirus (CMV).

In specific embodiments, the infecting microorganism is a protozoa, including, but not limited to *Giardia*.

In these embodiments, the antimicrobial peptides administered, preferably as a component of a pharmaceutical composition, can include a single peptide of Tables 1 or 5, or multiple peptides of Tables 1 and/or 5. The peptides may include peptides having at least 85%, or at least 90%, or at least 95% homology to a peptide sequence of those peptides set forth in Tables 1 and 5, and which effectively treat or prevent a microbial infection. The peptides may include fragments of the peptides of Tables 1 and 5 that retain the ability to effectively treat or prevent a microbial infection.

The peptides may include peptides having at least one amino acid substitution of SEQ ID NOs: 3-5 and 7-9, and which retain the antimicrobial activity of D-Dermaseptin S4 and/or D-Piscidin 1. An exemplary peptide includes the amino acid sequence set forth in SEQ ID NO:9. Appropriate peptides to use in the methods disclosed herein can be determined by those skilled in the art.

Therapeutical AMPs of this disclosure can be administered by a number of routes, including parenteral administration, for example, orally, topically, intravenous, intraperitoneal, intramuscular, intradermal, intrasternal, or intraarticular injection, or infusion. One of skill in the art can readily determine the appropriate route of administration.

The therapeutically effective amounts of the AMPs of this disclosure that inhibit or kill an infecting microorganism will be dependent upon the subject being treated, the severity and type of the infection, and the manner of administration. For example, a therapeutically effective amount of a peptide of this disclosure can vary from about 1 µg/injection up to about 10 mg/injection. The exact amount of the peptide is readily determined by one of skill in the art based on the age, weight, sex, and physiological condition of the subject. Effective doses can be extrapolated from dose-response curves derived from in vitro or animal model test systems.

In one embodiment, one or more peptides of this disclosure that effectively inhibit or kill an infecting microorganism can be administered in conjunction with one or more additional pharmaceutical agents. The additional pharmaceutical agents can be administered at the same time as, or sequentially with, the peptide(s) of this disclosure. In one embodiment, the additional pharmaceutical agent is an additional antimicrobial agent. When administered at the same time, the additional pharmaceutical agent(s) can be formulated in the same composition that includes the peptide(s) of this disclosure.

Those skilled in the art can determine an appropriate time and duration of therapy that includes the administration of a peptide of this disclosure to achieve the desired preventative or ameliorative effects on the subject treated.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

Example 1

In this Example, certain compositions and methods of antimicrobial peptides are described which demonstrate activity and improved therapeutic indices against bacterial pathogens.

2. Experimental Section 2.1. Peptide Synthesis and Purification

Synthesis of the peptides was carried out by standard solid-phase peptide synthesis methodology using 9-fluorenylmethoxycarbonyl (Fmoc) chemistry and 4-methylbenzhydrylamine hydrochloride (MBHA) resin using a CEM Liberty microwave peptide synthesizer, followed by the cleavage of the peptide from the resin. Peptide purification was performed by reversed-phase high-performance liquid chromatography (RP-HPLC) on a Zorbax 300 SB-C8 column (250×9.4 mm I.D.; 6.5 µm particle size, 300 Å pore size; Agilent Technologies, Little Falls, Del., USA) with a linear AB gradient at a flow rate of 2 mL/min, where eluent A was 0.2% aqueous trifluoroacetic acid (TFA), pH 2, and eluent B was 0.18% TFA in acetonitrile. The crude sample was loaded onto the column in 0.2% TFA, pH 2, followed by a 1% acetonitrile/min gradient to the point where a shallow 0.1% acetonitrile/min gradient started 12% below the acetonitrile concentration required to elute the peptide on injection of analytical sample using a gradient of 1% acetonitrile/min. The 0.1% acetonitrile/min gradient was run for 170 min. Fractions of 4 mL were collected and fraction analyses on an analytical column (as described below) were carried out and the appropriate fractions were pooled and freeze-dried to obtain pure peptide.

2.2. Analytical RP-HPLC and Temperature Profiling of Peptides

The purity of the peptides was verified by analytical RP-HPLC and the peptides were characterized by mass spectrometry (LC/MS). Crude and purified peptides were analyzed on an Agilent 1100 series liquid chromatograph (Little Falls, Del., USA). Analytical runs were performed on a Zorbax 300 SB-C8 column (150×2.1 mm I.D.; 5 µm particle size, 300 Å pore size) from Agilent Technologies using a linear AB gradient (1% acetonitrile/min) and a flow rate of 0.25 mL/min, where eluent A was 0.2% aqueous TFA, pH 2, and eluent B was 0.18% TFA in acetonitrile. Temperature profiling analyses were performed on the same column in 3° C. increments, from 5° C. to 80° C. using a linear AB gradient of 0.5% acetonitrile/min.

2.3. Characterization of Helical Structure

The mean residue molar ellipticities of peptides were determined by circular dichroism (CD) spectroscopy, using a Jasco J-815 spectropolarimeter (Jasco Inc. Easton, Md., USA) at 5° C. under benign (non-denaturing) conditions (50 mM $NaH_2PO_4/Na_2HPO_4$/100 mM KCl, pH 7.0), hereafter referred to as benign buffer, as well as in the presence of an α-helix inducing solvent, 2,2,2-trifluoroethanol, TFE, (50 mM $NaH_2PO_4/Na_2HPO_4$/100 mM KCl, pH 7.0 buffer/50% TFE). A 10-fold dilution of an approximately 500 µM stock solution of the peptide analogs was loaded into a 0.1 cm quartz cell and its ellipticity scanned from 195 to 250 nm. Peptide concentrations were determined by amino acid analysis.

2.4. Determination of Peptide Amphipathicity

Amphipathicity of peptides was determined by the calculation of hydrophobic moment, using the software package Jemboss version 1.2.1, modified to include a hydrophobicity scale. The hydrophobicity scale used in this study is listed as follows. Trp, 33.0; Phe, 30.1; Leu, 24.6; Ile, 22.8; Met, 17.3; Tyr, 16.0; Val, 15.0; Pro, 10.4; Cys, 9.1; His, 4.7; Ala, 4.1; Thr, 4.1; Arg, 4.1; Gln, 1.6; Ser, 1.2; Asn, 1.0; Gly, 0.0; Glu, −0.4; Asp, −0.8 and Lys, −2.0. These hydrophobicity coefficients were determined from RP-HPLC at pH 7 (10 mM $PO_4$ buffer containing 50 mM NaCl) of a model random coil peptide with a single substitution of all 20 naturally occurring amino acids. This HPLC-derived scale reflects the relative difference in hydophilicity/hydrophobicity of the 20 amino acid side-chains in an accurate manner.

2.5. Gram-Negative Bacteria Strains

All the *A. baumannii* strains used were (1) obtained from the collection of Dr. Anthony A. Campagnari at the University of Buffalo and originally isolated from different patients and organs/tissues (strain 649, blood; strain 689, groin; strain 759, gluteus; strain 821, urine; strain 884, axilla; strain 899, perineum; strain 964, throat; strain 985, pleural fluid and strain 1012, sputum); or (2) were purchased from the American Type Culture Collection (ATCC, Manassas, Va.) (strain ATCC 17978, fatal meningitis; and strain ATCC 19606, urine).

*P. aeruginosa* strains used are as follows; strain PAO1 was isolated from a human wound in 1955 in Australia; strain WR5 was isolated from a burn patient at Walter Reed Army Hospital, Washington, D.C., in 1976 and is a natural toxA mutant, but is virulent in experimental mouse models; strain PAK was originally isolated at Memorial University, St. John's, Newfoundland, Canada, and is widely used in the analysis of pili; strain PAM was originally isolated as a clinical isolate in 1995 at the Massachusetts General Hospital, Boston, and is virulent in a variety of plant and animal models of infection; strain M2 was originally isolated in 1975 from the gastrointestinal tract of a healthy CF1 mouse, University of Cincinnati College of Medicine, and Shriners Burns Institute, Cincinnati, Ohio, and is virulent in a burn mouse model of *P. aeruginosa* infection; and strain CP204 was isolated from a cystic fibrosis patient in 1989 at the National Jewish Medical and Research Center, Denver, Colo. All strains have been maintained at −80° C. in the laboratory of Michael Vasil, University of Colorado, School of Medicine.

2.6. Measurement of Antimicrobial Activity (MIC)

MICs were determined by a standard microtiter dilution method in Mueller Hinton (MH) medium. Briefly, cells were grown overnight at 37° C. in MH broth and were diluted in the same medium. Serial dilutions of the peptides were added to the microtiter plates in a volume of 50 µl, followed by the addition of 50 µl of bacteria to give a final inoculum of $5 \times 10^5$ colony-forming units (CFU)/mL. The plates were incubated at 37° C. for 24 h, and the MICs were determined as the lowest peptide concentration that inhibited growth.

2.7. Measurement of Hemolytic Activity ($HC_{50}$)

Peptide samples (concentrations determined by amino acid analysis) were added to 1% human erythrocytes in phosphate-buffered saline (100 mM NaCl, 80 mM $Na_2HPO_4$, 20 mM $NaH_2PO_4$, pH 7.4) and the reaction mixtures were incubated at 37° C. for 18 h in microtiter plates. Two-fold serial dilutions of the peptide samples were carried out. This determination w as made by withdrawing aliquots from the hemolysis assays and removing unlysed erythrocytes by centrifugation (800×g). Hemoglobin release was determined spectrophotometrically at 570 nm. The control for 100% hemolysis was a sample of erythrocytes treated with water or 0.1% Triton-X 100. The control for no release of hemoglobin w as a sample of 1% erythrocytes without any peptide added. Since erythrocytes were in an isotonic medium, no detectable release (<1% of that released upon complete hemolysis) of hemoglobin was observed from this control during the course of the assay. The hemolytic activity was determined as the peptide concentration that caused 50% hemolysis of erythrocytes after 18 h ($HC_{50}$). $HC_{50}$ was determined from a plot of percent lysis versus peptide concentration (μM) The inventors also determined the hemolytic activity after 1 hour at 37° C.

2.8. Calculation of Therapeutic Index ($HC_{50}$/MIC Ratio)

The therapeutic index is a widely accepted parameter to represent the specificity of antimicrobial peptides for prokaryotic versus eukaryotic cells. It is calculated by the ratio of $HC_{50}$ (hemolytic activity) and MIC (antimicrobial activity); thus, larger values of therapeutic index indicate greater specificity for prokaryotic cells.

3. Results 3.1. Peptide Design and Specificity Determinant(s)

Figure 2:
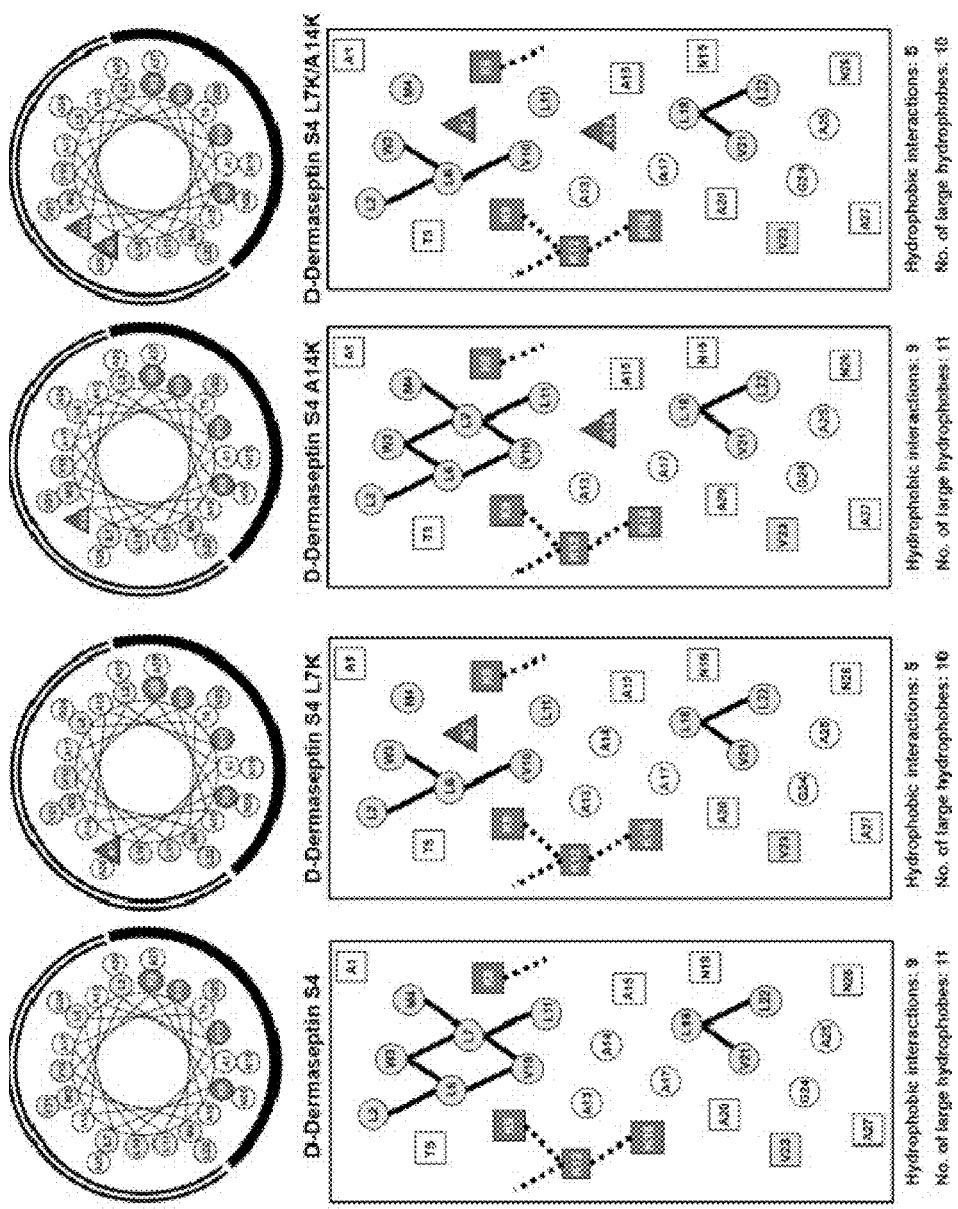
FIG. 2 shows helical wheel (upper panel) and helical net (lower panel) representation of D-Dermaseptin S4 and analogs, which are listed in Table 1. The one-letter code is used for amino acid residues. 'D' denotes that all residues in the peptides are in the D conformation. Positively charged residues (Lys and Arg) are darkly shaded on the right side of the helical wheel and the upper portion of the helical net. Large hydrophobes (Val, Ile, Leu and Phe) are lightly shaded on the upper and left side of the helical wheel and both the upper and lower portions of the helical net. The "specificity determinant" amino acid change is denoted by shaded triangles in the three D-Dermaseptin S4 analogs of the invention. In the helical wheel, the non-polar face is indicated as an open arc and the polar face is shown as a solid arc. In the helical net, the residues on the polar face are boxed and the residues on the non-polar face are circled. The i→i+3 and i→i+4 potential hydrophobic interactions along the helix are shown as black bars. The i→i+3 and i→i+4 potential electrostatic repulsions between positively charged residues along the helix are shown as dotted bars.

The inventors designed and synthesized nine antimicrobial peptides (all-D versions) including the native sequences, D-Piscidin 1 and a 27-residue version of D-Dermaseptin S4 (which was originally described as a 28-mer), which has a deletion of Ala 18 in the sequence of the 28-mer. This included 4 analogs of D-Piscidin 1 and 3 analogs of D-Dermaseptin S4 as shown in Table 1. FIGS. 1 and 2 show the amino acid sequences in helical wheel and helical net representations. The positively charged lysine or arginine residues are darkly shaded and are located on the polar face of the AMP. The large hydrophobes (Val, lie, Leu, Met, Phe and Trp) are lightly shaded and are located on the non-polar face of the AMP. The only exception is V23 in Dermaseptin S4 which is located in the polar face. However, there is only one large hydrophobe on the polar face compared to ten large hydrophobes on the non-polar face.

The positively charged residue(s) in the non-polar face ("specificity determinant(s)") are denoted as shaded triangles. The potential i to i+3/i to i+4 electrostatic repulsions between positively charged residues are shown as black dotted lines. The z to i+3/i to i+4 hydrophobic interactions between large hydrophobes are shown as solid black lines. These representations allow easy comparison of different analogs to explain their biological and biophysical properties described below.

The design concept of "specificity determinant(s)" (positively charged lysine residue(s) in non-polar face of α-helical AMPs) is developed in applications herein to achieve AMPS with useful attributes. In embodiments, the following biophysical and biological properties are achieved: (i) decreased number of hydrophobic interactions and disruption of the continuous hydrophobic surface that stabilizes the helical structure of the AMP; (ii) reduction of the hydrophobicity on the non-polar face and overall hydrophobicity; (iii) prevention of peptide self-association in aqueous conditions; (iv) dramatically reduced hemolytic activity; (v) maintained or enhanced antimicrobial activity and (vi) dramatically improved therapeutic index. The "specificity determinant" can allow the antimicrobial peptides of the invention to discriminate between eukaryotic and prokaryotic cell membranes, that is, exhibit pronounced selectivity for prokaryotic cell membranes. The specificity determinant can also make broad spectrum AMPs selective for gram-negative bacteria.

The inventors have chosen α-helical D-Piscidin 1 and D-Dermaseptin S4 for use as frameworks to substitute one or two lysine residue(s) at different positions in the non-polar face (I9K, V12K and G13K for D-Piscidin 1 (FIG. 1) and L7K, A14K and L7K/A14K for D-Dermaseptin S4 (FIG. 2)) to investigate the effect of such "specificity determinant(s)" on their biophysical properties including hydrophobicity, amphipathicity, helicity and self-association (oligomerization) as well as their biological activities including antibacterial activities against six strains of P. aeruginosa, eleven strains of A. baumannii, and 20 strains of Staphylococcus aureus, and hemolytic activities to human red blood cells and therapeutic indices.

3.2. Peptide Hydrophobicity

Amphipathic α-helical AMPs must have a certain minimum hydrophobicity to penetrate the hydrophobic membrane of prokaryotic cells. Hydrophobicity is one of the design features to optimize in AMPs. It is generally accepted that increasing the hydrophobicity of the non-polar face of amphipathic α-helical AMPs will increase antimicrobial activity. However, the inventors' laboratory made a major contribution to understanding the role of hydrophobicity in antimicrobial and hemolytic activity. At relatively low levels of hydrophobicity on the non-polar face, an increase in peptide hydrophobicity caused an improvement in antimicrobial activity until an optimum hydrophobicity was reached, at which point further increases in hydrophobicity beyond this optimum resulted in a dramatic loss of antimicrobial activity. In other words, there is an optimal hydrophobicity window where decreases or increases in hydrophobicity outside this window cause significant decreases in antimicrobial activity.

However, this relationship is not observed with hemolytic activity where increasing hydrophobicity correlates with stronger hemolytic activity and no decrease in hemolytic activity is observed at high hydrophobicity where antimicrobial activity is dramatically decreased. The inventors have associated the decrease in antimicrobial activity with high hydrophobicity and strong peptide self-association, which prevents the AMP from passing through the capsule and cell wall in prokaryotic cells to reach the cytoplasmic membrane. Peptide dimers/oligomers are in their folded α-helical conformation and would be inhibited from passing through the capsule and cell wall to reach the target membranes. There are no polysaccharide-based cell walls in eukaryotic cells. Thus, increasing AMP hydrophobicity usually increases hemolytic activity on human red blood cells. The inventors' "specificity determinant(s)" disrupt α-helical structure in aqueous media and maintain an unfolded monomer which can more easily penetrate the capsule and cell w all of prokaryotic cells to reach the membrane where hydrophobicity of the membrane induces peptide folding into an α-helical structure and the AMP can now disrupt the membrane causing leakage and cell death. Thus, there is an optimum hydrophobicity for each AMP to have the best antimicrobial activity and the least hemolytic activity.

The inventors observed that substituting a large hydrophobe, isoleucine or valine (I9K or V12K), in the non-polar face of D-Piscidin 1 dramatically reduced overall hydrophobicity (more than 10 min as measured by RP-HPLC retention time (Table 2) and disrupted two (for D-Piscidin 1 V12K) or three (for D-Piscidin 119K) hydrophobic interactions between large hydrophobes that stabilize the hydrophobic surface of the helix (FIG. 1). However, switching the hydrophilic gly cine to lysine at position 13 (D-Piscidin G13K) had very little effect on overall hydrophobicity. The retention times were 76.4 min and 74.6 min for D-Piscidin 1 and D-Piscidin 1 G13K, respectively (Table 2). For D-Dermaseptin S4, a single leucine to lysine substitution at position 7 disrupted four hydrophobic interactions on the non-polar face (FIG. 2), thereby decreasing peptide overall hydrophobicity by more than 29 min (Table 2). A second "specificity determinant" at position 14 (D-Dermaseptin S4 L7K, A14K) further decreased hydrophobicity by almost 17 min, that is, a total decrease of 46 min from native D-Dermaseptin S4 (Table 2).

fact that most AMPs are highly amphipathic the inventors decided to investigate the biological and biophysical properties of the 27-residue version of D-Dermaseptin S4. Substituting with one or two lysine residues at positions 7 and 14 lowered the amphipathicity to 2.64 for D-Dermaseptin S4 L7K. and 2.42 for D-Dermaseptin S4 L7K, A14K. It should be noted that, although the overall amphipathicity is low, the helical region identified in the NMR studies (residues 1-14) has an amphipathicity value of 5.48 for native D-Dermaseptin S4 (1-14), 4.12 for D-Dermaseptin S4 (1-14) L7K and 3.76 for D-Dermaseptin S4 (1-14) L7K, A14K (Table 2). The amphipathicity of region 1-14 can explain the overall hydrophobicity of D-Dermaseptin S4 and its analogs. The specificity determinant(s) in the non-polar face decreased overall hydrophobicity and amphipathicity, but these molecules remained very amphipathic when in a helical conformation.

3.4. Secondary Structure of Peptides

FIG. 4 shows the CD spectra of the peptides in different environments (i.e., under benign conditions (non-denaturing) and in the buffer with 50% TFE (to mimic the hydrophobic environment of the membrane). It should be noted

TABLE 2

Biophysical data

| Peptide name | Net charge | Hydrophobicity $t_R^a$ (min) | Benign $[\theta]222^b$ | % Helix$^c$ | 50% TFE $[\theta]222^b$ | % Helix$^c$ | $P_A^d$ | Amphipathicity$^e$ |
|---|---|---|---|---|---|---|---|---|
| D-Piscidin 1 | +3 | 76.4 | 100 | <1 | 36,200 | 100 | 0.78 | 5.32 |
| D-Piscidin 1 I9K | +4 | 65.4 | −300 | <1 | 20,950 | 58 | 1.29 | 4.24 |
| D-Piscidin 1 V12K | +4 | 65.9 | −200 | <1 | 16,000 | 44 | 0.69 | 4.81 |
| D-Piscidin 1 G13K | +4 | 74.6 | −250 | <1 | 34,050 | 94 | 0.95 | 5.27 |
| D-Dermaseptin S4 | +4 | 124.4 | 28,900 | 75 | 38,400 | 100 | 12.61 | 3.58 (5.48) |
| D-Dermaseptin S4 L7K | +5 | 95.1 | 1,950 | 5 | 27,250 | 71 | 4.80 | 2.64 (4.12) |
| D-Dermaseptin S4 L7K,A14K | +6 | 78.6 | 2360 | 6 | 36,042 | 94 | 2.29 | 2.42 (3.76) |

$^a t_R$ denotes retention time in RP-HPLC at pH 2 and room temperature, and is a measure of overall peptide hydrophobicity.
$^b$ The mean residue molar ellipticities $[\theta]_{222}$ (deg cm$^2$/dmol) at wavelength 222 nm were measured at 5° C. in benign conditions (100 mM KCl, 50 mM NaH$_2$PO$_4$/Na$_2$HPO$_4$, pH 7.0) or in benign buffer containing 50% trifluoroethanol (TFE) by circular dichroism spectroscopy.
$^c$ The helical content (as a percentage) of a peptide relative to the molar ellipticity value of parent peptide (D-Piscidin 1 or D-Dermaseptin S4) in the presence of 50% TFE.
$^d P_A$ denotes self-association parameter (dimerization/oligomerization) of each peptide during RP-HPLC temperature profiling, which is the maximal retention time difference of $(t_R^t-t_R^5$ for peptide analogs)-$(t_R^t-t_R^5$ for control peptide C) within the temperature range $t_R^t-t_R^5$ is the retention time difference of a peptide at a specific temperature $(t_R^t)$ compared with that at 5° C. $(t_R^5)$. The sequence of the random coil control peptide C is shown in Table 1.
$^e$ Amphipathicity was determined by calculation of hydrophobic moment using hydrophobicity coefficients determined by reversed-phase chromatography; see methods for details. The amphipathicity values for D-Dermaseptin S4 and its analogs (residues 1-14) are shown in brackets.

3.3. Amphipathicity

Figure 3:
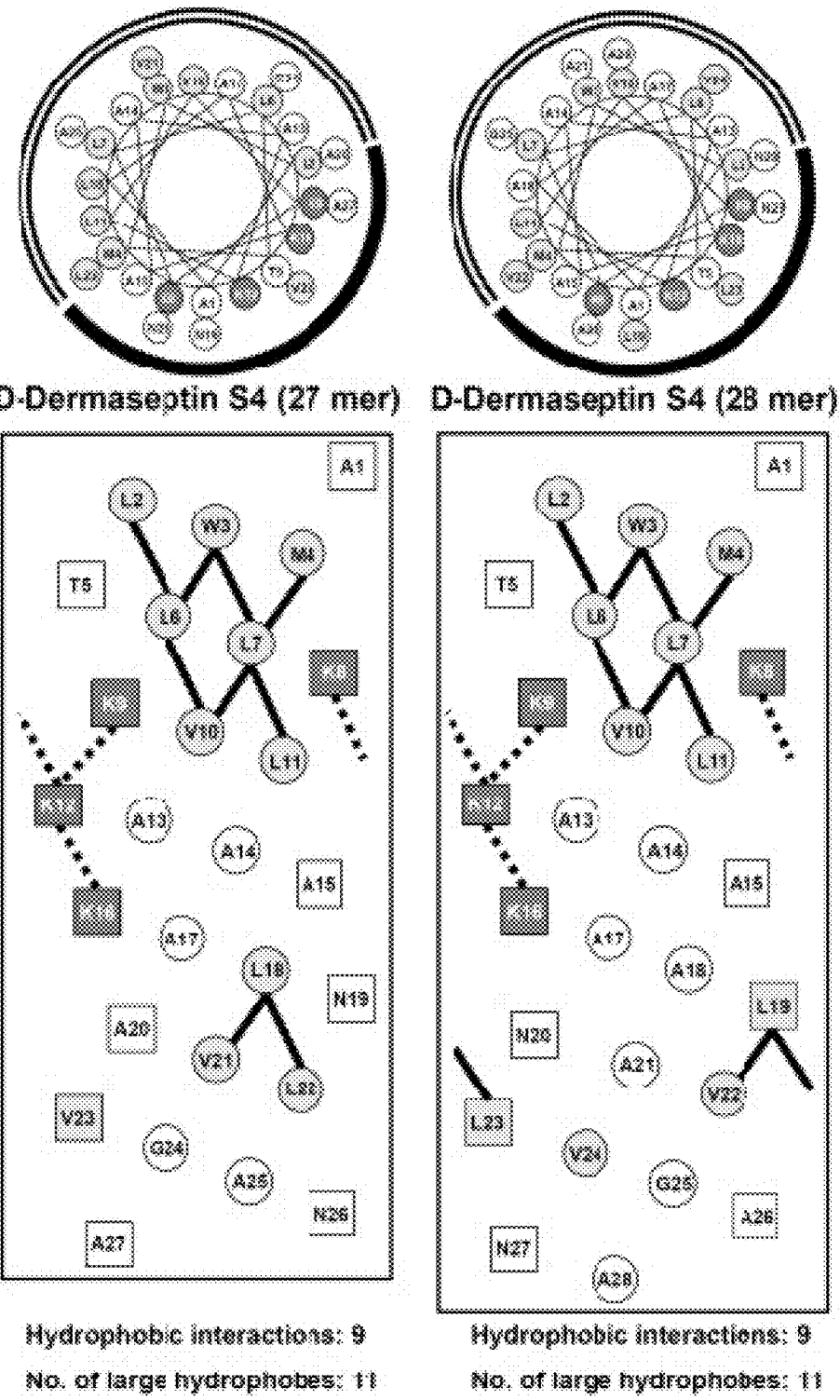
FIG. 3 shows Helical wheel (upper panel) and helical net (lower panel) representation of D-Dermaseptin S4 (27 mer) and D-Dermaseptin S4 (28 mer). The one-letter code is used for amino acid residues. 'D' denotes that all residues in the peptides are in the D conformation. Positively charged residues (Lys) are darkly shaded, while large hydrophobes (Val, Leu, Met and Trp) are lightly shaded. In the helical wheel, the non-polar face is indicated as an open arc and the polar face is shown as a solid arc. In the helical net, the residues on the polar face are boxed and the residues on the non-polar face are circled. The i→i+3 and i→i+4 potential hydrophobic interactions along the helix are shown as black bars. The i→i+3 and i→i+4 potential electrostatic repulsions between positively charged residues along the helix are shown as dotted bars.
Figure 4A:
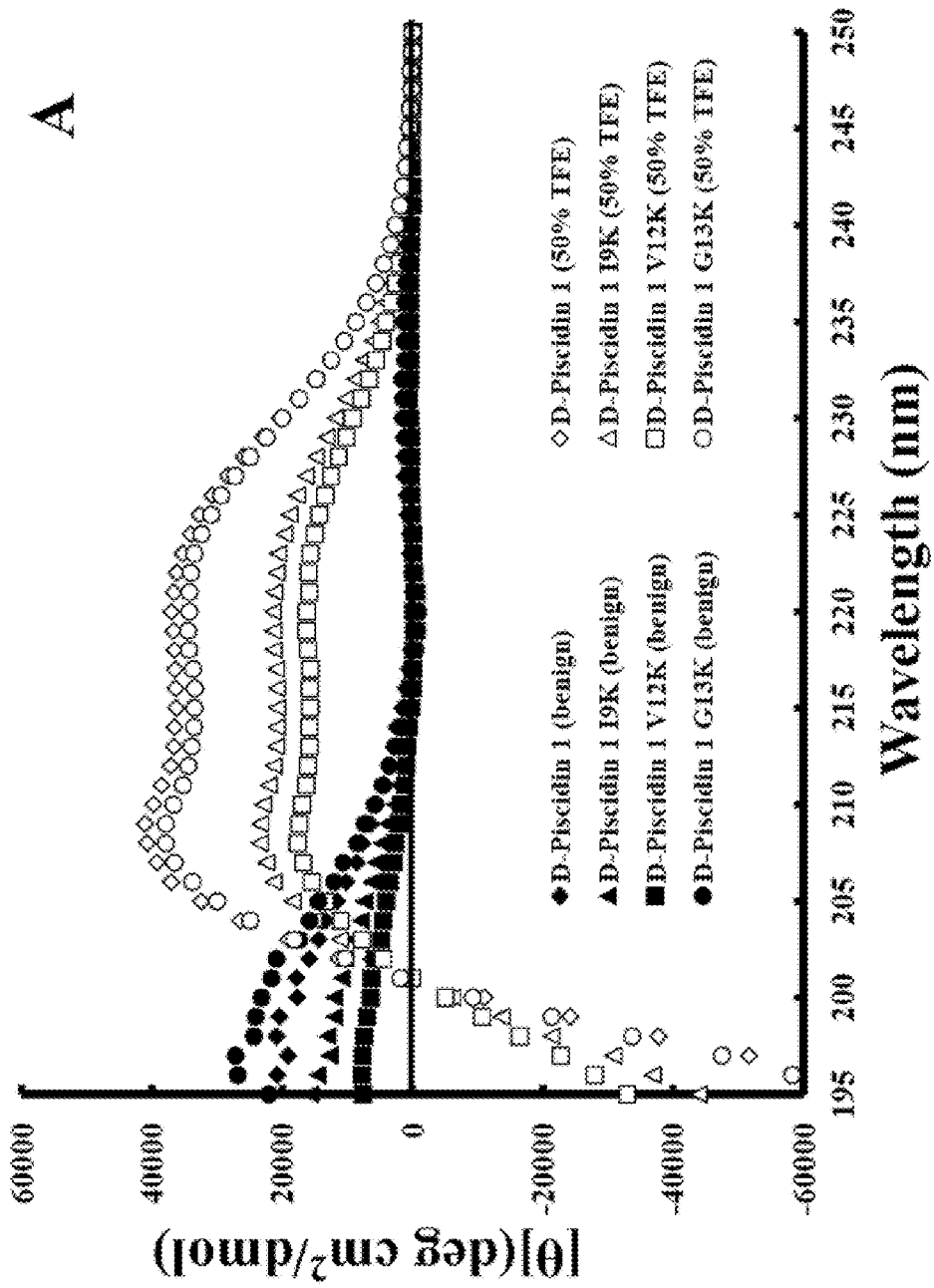
FIGS. 4A-4C show CD spectra of D-Pisicidin 1 and D-Dermaseptin S4 analogs of the invention.
Figure 4B:
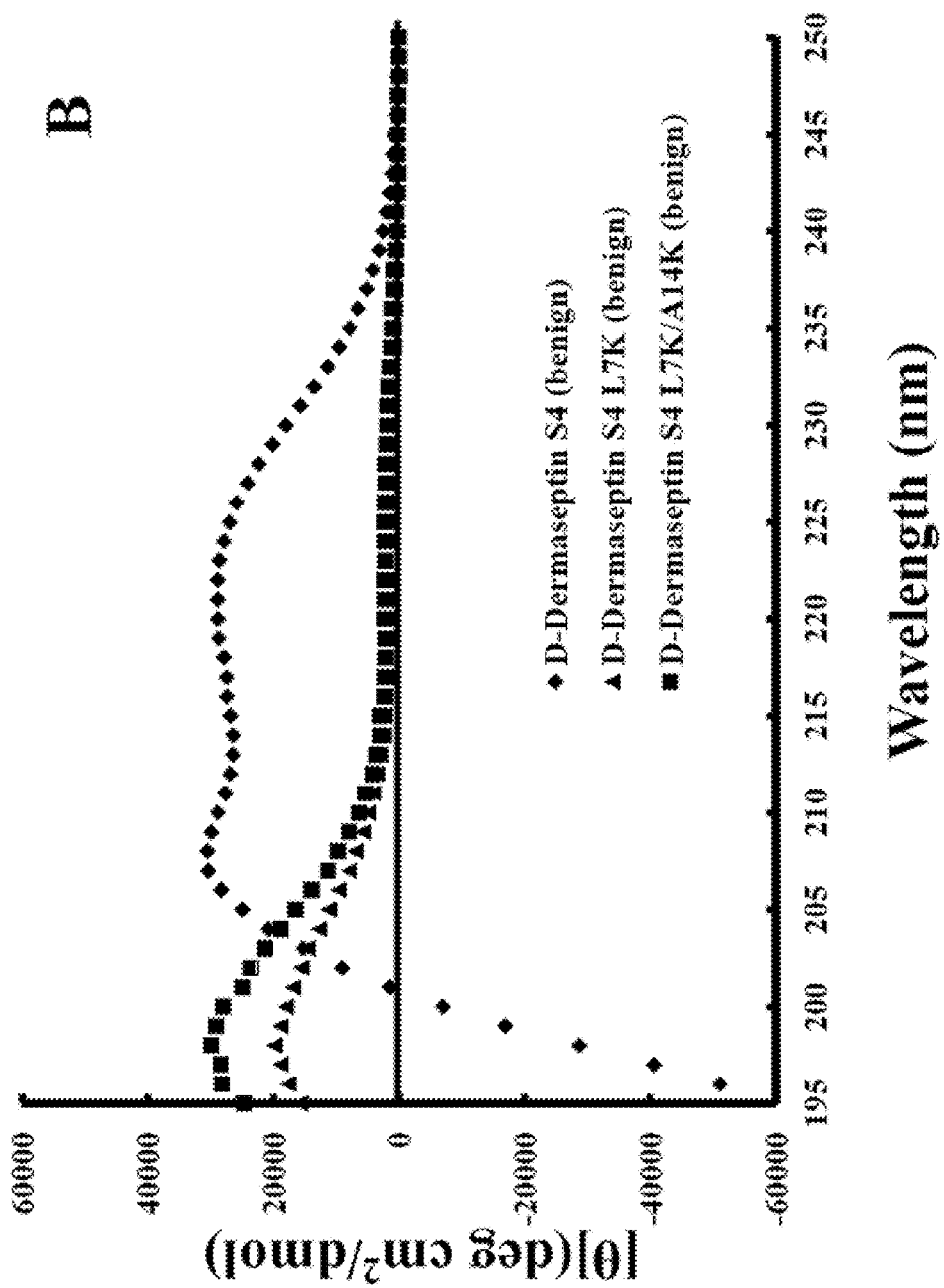
Figure 4C:
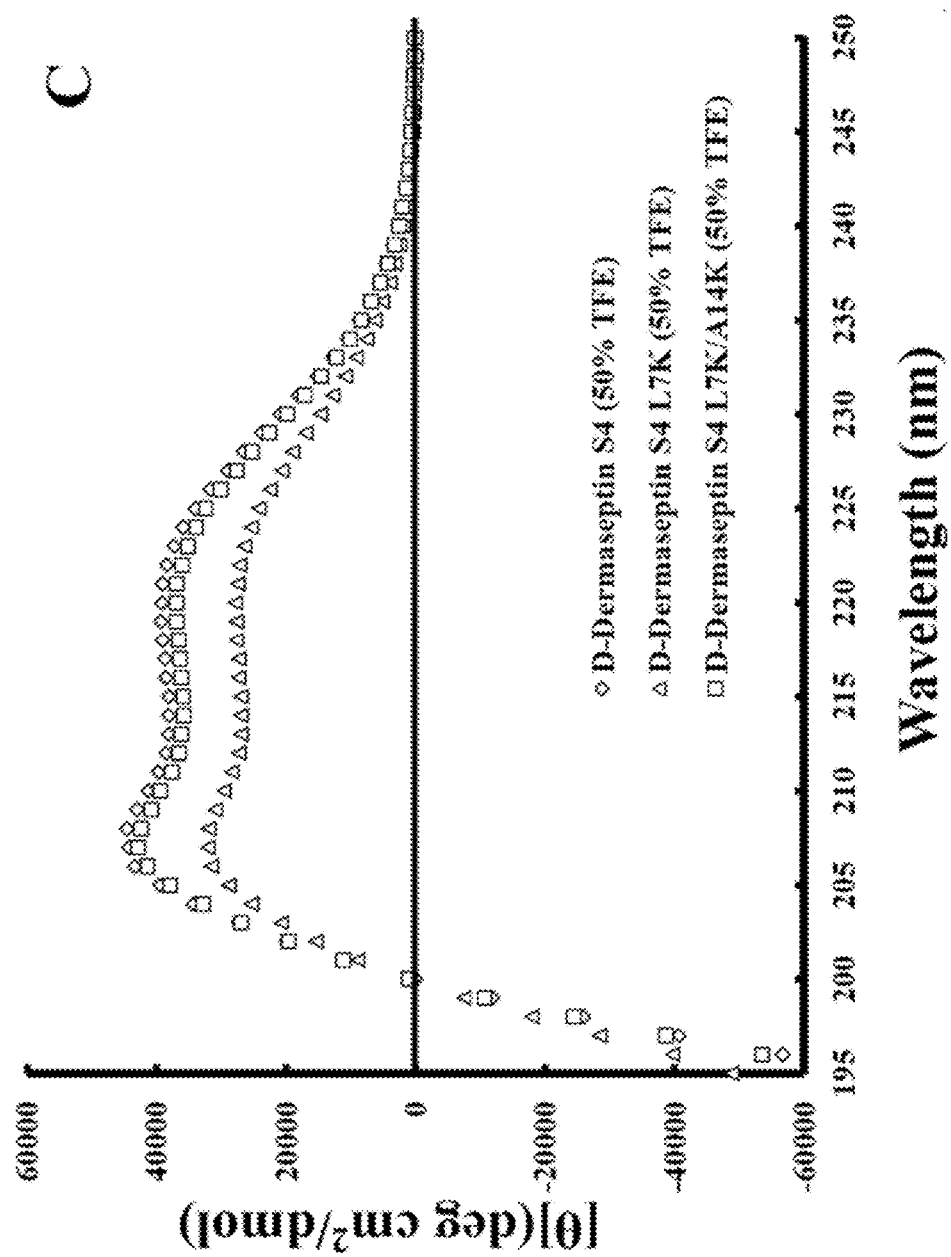

The native sequence of D-Piscidin 1 is very amphipathic with a value of 5.32 (Table 2). D-Piscidin 1 G13K, the analog where there was no loss of a hydrophobe on substitution of a lysine residue on the non-polar face, maintained the same level of amphipathicity with a value of 5.27. Substituting one large hydrophobe with lysine, lowered the amphipathicity of D-Piscidin 1 V12K and D-Piscdin 1 I9K to 4.81 and 4.24, respectively. However, these analogs with the single specificity determinant still remain very amphipathic. FIG. 3 shows a comparison of the 27- and 28-residue version of D-Dermaseptin S4. Of particular interest is that the deletion of Alai 8 from the 28-residue sequence dramatically changes the composition of the non-polar face. In the case of D-Dermaseptin S4 (28 mer) two hydrophobic Leu19 and Leu23 are located in the polar face (FIG. 3, right panel), whereas in the case of D-Dermaseptin S4 (27 mer) only a single hydrophobe Val23 remains located in the polar face (FIG. 3, left panel). This subtle change also has a large effect on the amphipathicity of the AMP. The amphipathicity values for D-Dermaseptin S4 (27 mer) and (28 mer) are 3.58 and 1.63, respectively. Due to this large difference and the that all-D α-helical peptides exhibited a positive spectrum. The helicities of the peptides in benign buffer and in 50% TFE relative to that of their native peptide (D-Piscidin 1 or D-Dermaseptin S4) in 50% TFE were determined (Table 2). All D-Piscidin 1 analogs showed negligible secondary structure in benign buffer (FIG. 4A closed symbols) and a typical α-helix spectrum with double maxima at 208 and 222 nm in the non-polar environment of 50% TFE, a mimic of hydrophobicity and the α-helix-inducing ability of the membrane (FIG. 4A open symbols). D-Piscidin 119K and D-Piscidin 1 V12K, the analogs with one large hydrophobe in the non-polar face replaced by lysine, showed, respectively, a 42% and 56% decrease in helicity in 50% TFE, while D-Piscidin 1 G13K, the analog where there was no loss of a hydrophobe on substitution of a lysine residue, showed only 6% reduction in helicity compared to that of the native sequence (Table 2). D-Dermaseptin S4 was 75% α-helical in benign medium and was completely induced to α-helical structure in the presence of 50% TFE. By comparison, the analogs D-Dermaseptin S4 L7K and D-Dermaseptin S4 L7K, A14K showed no α-helical structure in benign medium, indicating that lysine substitutions on the hydrophobic face completely disrupted α-helical structure (FIG. 4B). Helical structure can be induced in these two analogs in the presence of a hydrophobic environment (FIG. 4C).

The general effect of "specificity determinant(s)" in the context of certain peptides herein is to reduce or remove α-helical structure in benign media but allow induction of α-helical structure in the presence of the hydrophobicity of the membrane.

3.5 Peptide Self-Association

Peptide self-association (i.e., the ability to oligomerize/dimerize) in aqueous solution is a very important parameter for antimicrobial activity. The inventors assume that monomeric random-coil antimicrobial peptides are best suited to pass through a polysaccharide capsule, the outer membrane (i.e. lipopolysaccharide), and the cell wall (i.e. peptidoglycan) of microorganisms prior to penetration into the cytoplasmic membrane, induction of α-helical structure and disruption of membrane structure to kill target cells. Thus, if the self-association ability of a peptide in aqueous media is too strong (e.g., forming stable folded dimers/oligomers through interaction of their non-polar faces) this could decrease the ability of the peptide to dissociate to monomer where the dimer/oligomer cannot effectively pass through the capsule and cell wall to reach the membrane. The ability of the peptides in the present study to self-associate was determined by the technique of RP-HPLC temperature profiling at pH 2 over the temperature range of 5° C. to 80° C.

Figure 5:
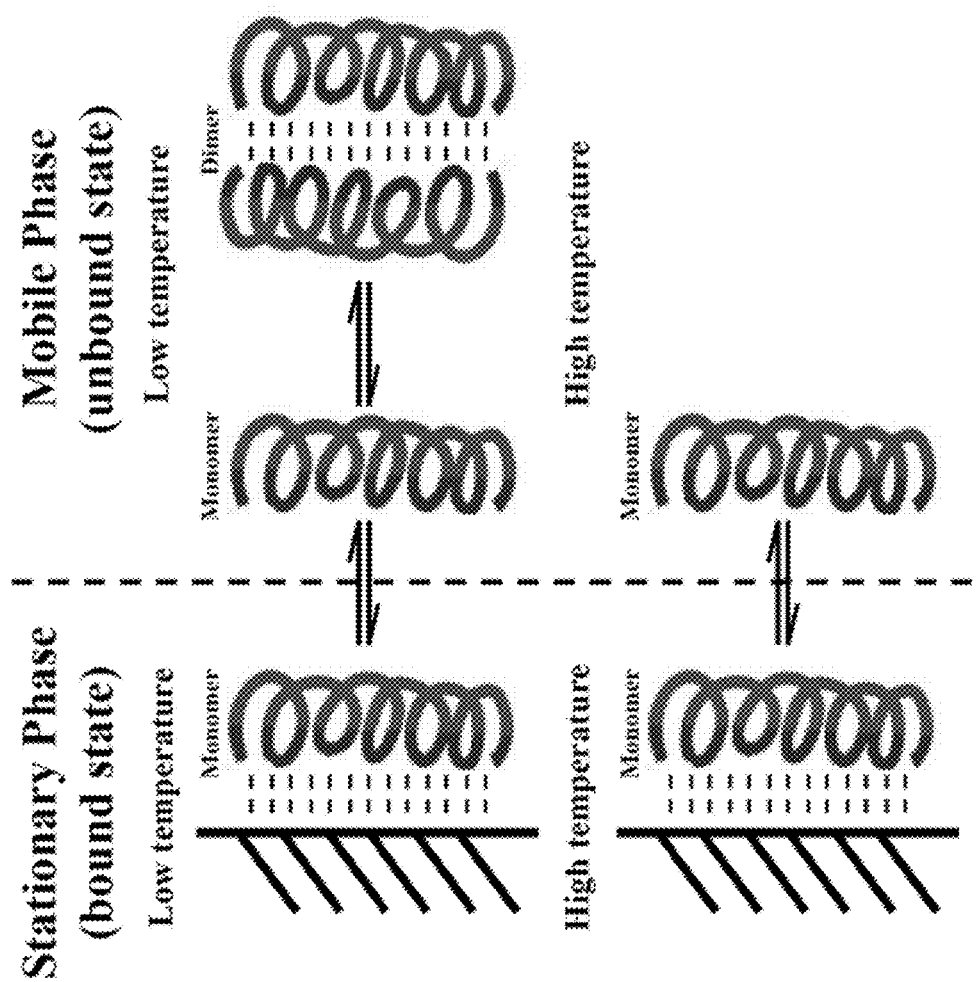
FIG. 5 shows a proposed mechanism for temperature profiling by RP-HPLC. Only the folded monomeric α-helix is bound to the hydrophobic reversed-phase matrix. During partitioning at low temperature, there is an equilibrium between monomer and dimer in the mobile phase. At some higher temperature during partitioning there is only monomer present in the mobile phase. This method measures the self-association parameter for any amphipathic molecule, as demonstrated for D-Dermaseptin S4 and its analogs in FIG. 6.

The inventors have worked to optimize improvement in the biological properties of AMPs, in part by understanding how the RP-HPLC temperature profiling method works. At low temperature, AMPs are capable of self-associating in aqueous solution via their non-polar faces. In the case of dimerization, equilibrium is established between monomer and dimer and the concentration of monomer and dimer at any given temperature depends on the strength of the hydrophobic interaction between the two monomers. In RP-HPLC, the hydrophobicity of the matrix disrupts/dissociates the dimer and only the monomeric form of the peptide is bound to the hydrophobic matrix by its non-polar face (preferred binding domain) (FIG. 5). Only the monomeric form of the AMP can partition between the alkyl ligands on the reversed-phase column and the mobile phase. At low temperature, the monomer can dimerize in the mobile phase and the retention time is decreased due to the large population of dimers in solution. At higher temperatures, the population of dimers in the mobile phase during partitioning decreases, thereby increasing the concentration of monomeric peptide in solution and thereby increasing retention time. At some higher temperature no dimer exists in the mobile phase and the peptide has the maximum retention time. With a random coil peptide that does not dimerize, the peptide binds to the stationary phase and partitions in the mobile phase as a monomer with undefined structure throughout the temperature range of 5° C. to 80° C. Thus, the effect of temperature on retention time is linear and decreases with increasing temperature.

FIG. 6A show's the retention behavior of D-Dermaseptin S4 and its peptide analogs after normalization to their retention times at 5° C. Control peptide C shows a linear decrease in retention time with increasing temperature and is representative of peptides which have no ability to self-associate during RP-HPLC. Control peptide C is a monomeric random coil peptide in both aqueous and hydrophobic media; thus, its linear decrease in peptide retention behavior with increasing temperature within the range of 5° C. to 80° C. represents only the general effects of temperature due to greater solute diffusivity and enhanced mass transfer between the stationary and mobile phase at higher temperatures. To allow for these general temperature effects, the data for the control peptide was subtracted from each temperature profile, as shown in FIG. 6B. Thus, the peptide self-association parameter, PA, represents the maximum change in peptide retention time relative to the random coil peptide C. Note that the higher the PA value, the greater the self-association. The inventors observed the pronounced effect where one "specificity determinant", L7K, dramatically decreased peptide self-association from 12.61 min for D-Dermaseptin S4 to 4.80 min for D-Dermaseptin S4 L7K (Table 2). Adding a second "specificity determinant" at position 14 (A14K) further lowered the association parameter PA value to 2.29 min for D-Dermaseptin S4 L7K, A14K. The self-association is totally different for D-Piscidin 1 and its analogs which all have very low PA values (0.69-1.29) compared to D-Dermaseptin S4 (Table 2).

Previous studies showed that the extreme toxicity of Dermaseptin S4 is probably related to its higher hydrophobicity and self-association ability, as both nuclear magnetic resonance and fluorescence methods have indicated that the peptide is in a high aggregation state in aqueous solutions, whereas sequential truncation of the N-terminal domain (hydrophobic stretch) of Dermaseptin S4 confirmed that such hydrophobic interactions between the N-terminus of Dermaseptin S4 monomers is primarily responsible for the peptide's oligomerization in solution. Self-association in solution is also probably responsible for limiting its spectrum of potential target cells. The dramatic decrease in self-association of D-Dermaseptin S4 L7K, A14K, compared to native D-Dermaseptin S4 correlates with the dramatic decrease in hemolytic activity of 402-fold (Table 4).

3.6. Antibacterial Activity

Antibacterial activities against six strains of *P. aeruginosa* and eleven strains of *A. baumannii* are compared in Table 3. Geometric mean of MIC values was calculated to provide an overall view of antimicrobial activity of different analogs. It is clear that the peptides the inventors have developed were effective in killing the microorganisms tested. Compared to a dramatic reduction in hemolytic activity, antibacterial activity of D-Piscidin 1 and D-Dermaseptin S4 analogs against eleven strains of *A. baumannii* maintained the same level of efficacy (within 2-fold) upon the substitution of "specificity determinant(s)" (Table 3).

TABLE 3

Antimicrobial activity of D-piscidin 1 and D-dermaseptin S4 analogs against gram negative bacteria. Values are MIC$^a$ (µM).

A. Antimicrobial activity against *Acinetobacter baumannii*

| Peptide | Strain | | | | | | | | | | | | GM$^b$ | Fold$^c$ |
|---|---|---|---|---|---|---|---|---|---|---|---|---|---|---|
| | ATCC 17978 | ATCC 19606 | 649 | 689 | 759 | 821 | 884 | 899 | 964 | 985 | 1012 | | | |
| | Source | | | | | | | | | | | | | |
| | Fatal meningitis | Urine | Blood | Groin | Gluteus | Urine | Axilla | Perineum | Throat | Pleural fluid | Sputum | | | |
| D-Piscidin 1 | 3.0 | 3.0 | 3.0 | 1.5 | 3.0 | 3.0 | 3.0 | 3.0 | 3.0 | 1.5 | 6.1 | 2.8 | 1.0 |
| D-Piscidin 1 G13K | 5.9 | 5.9 | 3.0 | 5.9 | 5.9 | 5.9 | 5.9 | 5.9 | 5.9 | 3.0 | 5.9 | 5.2 | 0.5 |
| D-Piscidin 1 V12K | 3.0 | 3.0 | 3.0 | 3.0 | 3.0 | 3.0 | 3.0 | 3.0 | 3.0 | 1.5 | 3.0 | 2.8 | 1.0 |
| D-Piscidin 1 I9K | 3.0 | 1.5 | 3.0 | 3.0 | 3.0 | 3.0 | 3.0 | 3.0 | 3.0 | 3.0 | 6.0 | 3.0 | 0.9 |
| D-Dermaseptin S4 | 2.8 | 2.8 | 1.4 | 1.4 | 1.4 | 2.8 | 2.8 | 1.4 | 1.4 | 0.7 | 2.8 | 1.8 | 1.0 |
| D-Dermaseptin S4 L7K | 0.7 | 0.4 | 0.7 | 0.7 | 0.4 | 0.4 | 1.4 | 0.4 | 2.8 | 0.7 | 1.4 | 0.7 | 2.6 |
| D-Dermaseptin S4 L7K,A14K | 0.7 | 0.7 | 0.7 | 0.7 | 1.4 | 0.7 | 1.4 | 1.4 | 2.7 | 0.7 | 2.7 | 1.1 | 1.6 |

B. Antimicrobial activity against *Pseudomonas aeruginosa*. Values are MIC$^a$ (µM).

| Peptide | Strain | | | | | | GM$^b$ | Fold$^c$ |
|---|---|---|---|---|---|---|---|---|
| | PAO1 | PAK | PA14 | CP204 | M2 | WR5 | | |
| | Source | | | | | | | |
| | Human wound | — | — | Cystic fibrosis patient | Burn mouse model | Burn patient | | |
| D-Piscidin 1 | 24.3 | 12.2 | 24.3 | 24.3 | 24.3 | 12.2 | 19.3 | 1.0 |
| D-Piscidin 1 G13K | 23.7 | 11.8 | 23.7 | 47.3 | 11.8 | 23.7 | 21.1 | 0.9 |
| D-Piscidin 1 V12K | 24.0 | 6.0 | 24.0 | 24.0 | 24.0 | 12.0 | 17.0 | 1.1 |
| D-Piscidin 1 I9K | 48.3 | 12.1 | 24.2 | 48.3 | 48.3 | 74.2 | 10.5 | 0.6 |
| D-Dermaseptin S4 | 11.3 | 11.3 | 22.5 | 11.3 | 11.3 | 11.3 | 12.6 | 1.0 |
| D-Dermaseptin S4 L7K | 2.8 | 2.8 | 2.8 | 2.8 | 2.8 | 2.8 | 2.8 | 4.5 |
| D-Dermaseptin S4 L7K,A14K | 5.5 | 1.4 | 5.5 | 1.4 | 21.9 | 11.0 | 4.9 | 2.6 |

$^a$MIC is minimal inhibitory concentration (µM) that inhibited growth of different strains in Mueller-Hinton (MB) medium at 37° C. after 24 h. MIC is given based on three sets of determinations;
$^b$GM is the geometric mean of the MIC values from 11 differein isolates of *A. baumannii* or 6 different isolates of *P. aeruginosa*;
$^c$The fold improvement in antimicrobial activity (geometric mean data) compared to that of native D-piscidin 1 or D-dermaseptin S4.

3.7. Hemolytic Activity

Figure 7:
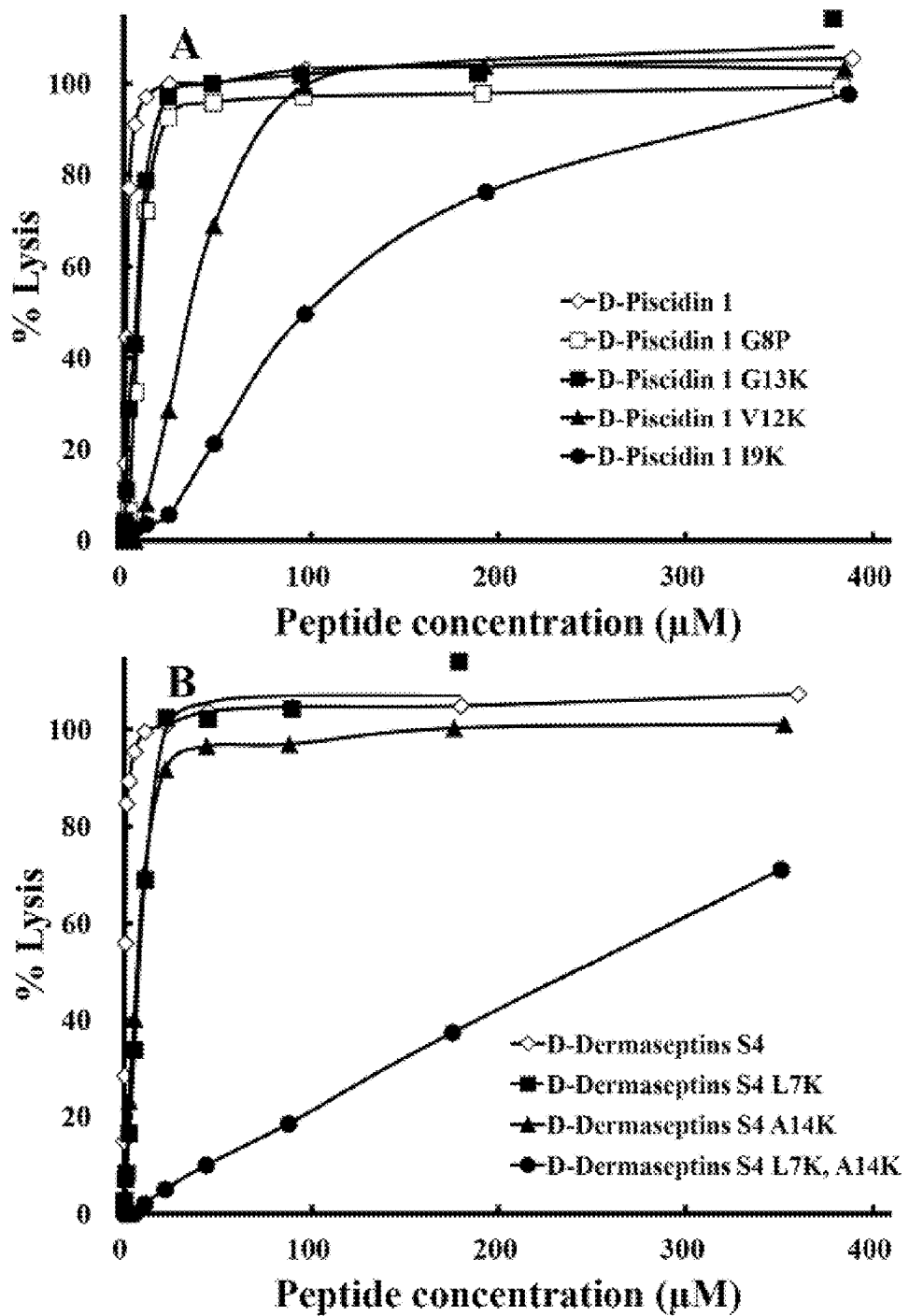
FIG. 7 shows the hemolytic activity of peptide D-Piscidin 1 and analogs (panel A of FIG. 7) and D-Dermaseptin S4 and analogs (panel B of FIG. 7) after 18 hours of incubation time at 37° C. The concentration-response curves of peptides for percentage lysis of human red blood cells (hRBC) are shown. The control for 100% hemolysis was a sample of erythrocytes treated with water. The peptide concentration is reported as micromolar (µM).

The hemolytic activities of the peptides against human erythrocytes were determined as a measure of peptide toxicity toward higher eukaryotic cells. The effect of peptide concentration on erythrocyte hemolysis is shown in FIG. 7. From these plots, the HC$_{50}$ values, the peptide concentration that produces 50% hemolysis of human red blood cells after 18 hours in the standard microtiter dilution method was determined.

Figure 6:
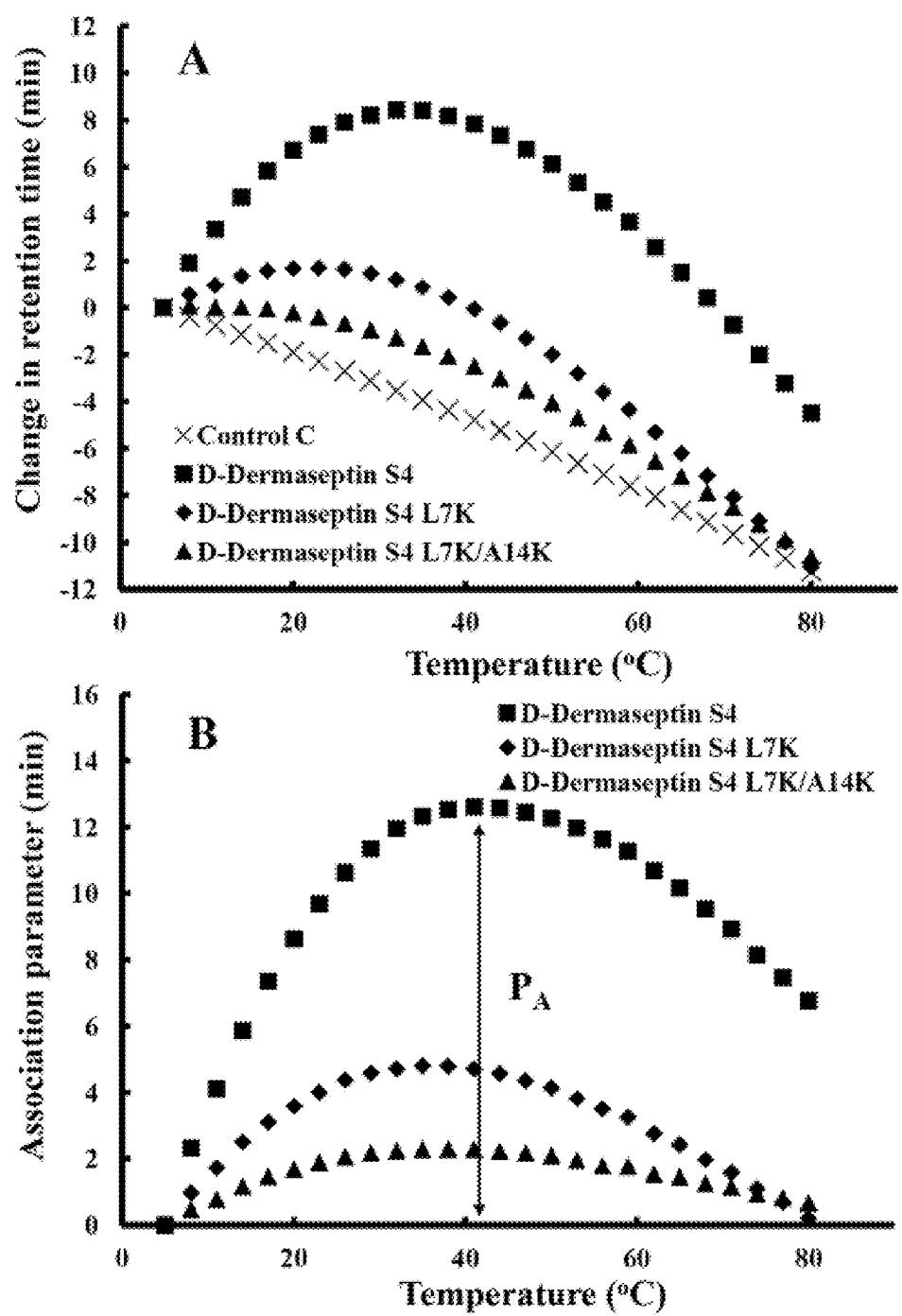
FIG. 6 shows D-Dermaseptin S4 analogs self-association ability as monitored by temperature profiling in RP-HPLC. In panel A of FIG. 6, the retention times of peptides are normalized to 5° C. through the expression $(t_R^1-t_R^5)$, where $t_R^1$ is the retention time at a specific temperature of an antimicrobial peptide or control peptide C, and $t_R^5$ is the retention time at 5° C. In panel B of FIG. 6, the retention behavior of the peptides was normalized to that of control peptide C through the expression $(t_R-t_R^5$ for peptides$)-(t_R^1-t_R^5$ for control peptide C$)$. The maximum change in retention time from the control peptide C defines the peptide association parameter, denoted PA (Table 2). The sequences of the peptides and the random coil control peptide (C) are shown in Table 1.

A single "specificity determinant" had a dramatic effect in lowering the hemolytic activity of D-Piscidin 1 from HC$_{50}$ value of 1.8 µM to 98 µM for D-Piscidin 1 I9K, a 54-fold improvement (Table 4). Similarly, a single "specificity determinant" lowered the hemolytic activity of D-Dermaseptin S4 from a HC$_{50}$ value of 0.6 µM to 8.6 µM for D-Dermaseptin S4 L7K, a 14-fold improvement (Table 4) and 7 µM for D-Dermaseptin S4 A14K, an 11.7-fold improvement (FIG. 7). The addition of a second "specificity determinant" in D-Dermaseptin S4 to give the analog D-Dermaseptin S4 L7K,A14K decreased the hemolytic activity from 0.6 µM to a HC$_{50}$ value of 241 µM, a 402-fold improvement in hemolytic activity. This also suggests a synergistic effect of having two "specificity determinants". These two lysine residues also systematically lowered the self-association parameter (FIG. 6).

TABLE 4

Summary of biological activity of D-Piscidin 1 and D-Dermaseptin S4 analogs

| Peptide Name | Hemolytic activity | | Antimicrobial activity | | | | | |
|---|---|---|---|---|---|---|---|---|
| | | | *Acinetobacter baumannii* | | | *Pseudomonas aeruginosa* | | |
| | HC$_{50}$$^a$ (µM) | Fold$^b$ | MIC$_{GM}$$^c$ (µM) | T.I.$^d$ | Fold$^c$ | MIC$_{GM}$$^c$ (µM) | T.I.$^d$ | Fold$^c$ |
| D-Piscidin 1 | 1.8 | 1.0 | 2.8 | 0.6 | 1.0 | 19.3 | 0.1 | 1.0 |
| D-Piscidin 1 G13K | 7.0 | 3.9 | 5.2 | 1.3 | 2.2 | 21.1 | 0.3 | 3.0 |
| D-Piscidin 1 V12K | 35 | 19 | 2.8 | 13 | 22 | 17.0 | 2.1 | 21 |
| D-Piscidin 1 I9K | 98 | 54 | 3.0 | 33 | 55 | 30.5 | 3.2 | 32 |

TABLE 4-continued

Summary of biological activity of D-Piscidin 1 and D-Dermaseptin S4 analogs

| | Hemolytic activity | | Antimicrobial activity | | | | | |
| --- | --- | --- | --- | --- | --- | --- | --- | --- |
| | | | *Acinetobacter baumannii* | | | *Pseudomonas aeruginosa* | | |
| Peptide Name | $HC_{50}{}^a$ (μM) | Fold[b] | $MIC_{GM}{}^c$ (μM) | T.I.[d] | Fold[e] | $MIC_{GM}{}^c$ (μM) | T.I.[d] | Fold[e] |
| D-Dermaseptin S4 | 0.6 | 1.0 | 1.8 | 0.3 | 1.0 | 12.6 | 0.05 | 1.0 |
| D-Dermaseptin S4 L7K | 8.6 | 14 | 0.7 | 12 | 40 | 2.8 | 3.1 | 62 |
| D-Dermaseptin S4 L7K,A14K | 241 | 402 | 1.1 | 219 | 730 | 4.9 | 49 | 980 |

[a] $HC_{50}$ is the concentration of peptide (μM) that results in 50% hemolysis after 18 hours at 37° C. The analogs with the best $HC_{50}$ values are bolded.
[b] The fold improvement in $HC_{50}$ compared to that of D-Piscidin 1 or D-Dermaseptin S4. The analogs with the best fold improvements are bolded.
[c] MIC is the minimum inhibitory concentration (μM) of peptide that inhibits growth of bacteria after 24 hours at 37° C. $MIC_{GM}$ is the geometric mean of the MIC values from 11 different isolates of *A. baumarmii* or 6 different isolates of *P. aeruginosa*.
[d] T.I. denotes therapeutic index, which is the ratio of the $HC_{50}$ value (μM) over the geometric mean MIC value (μM). Large values indicate greater antimicrobial specificity. The analogs with the best therapeutic indices are bolded.
[e] The fold improvement in therapeutic index compared to that of D-Piscidin 1 or D-Deimaseptin S4. The analogs with the best fold improvements are bolded.

Figure 8:
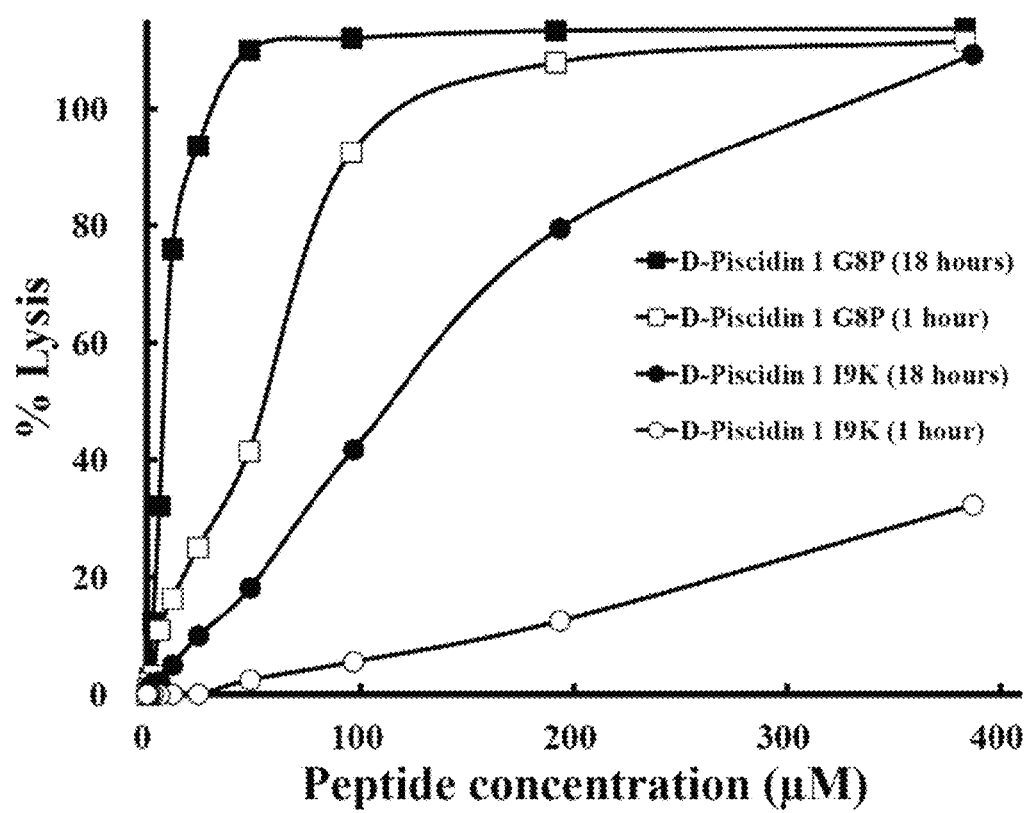
FIG. 8 shows the comparison of hemolytic activity of peptide D-Piscidin 1 G8P and D-Piscidin 119K after 1 hour or 18 hours treatment. The concentration-response curves of peptides for percentage lysis of human red blood cells (hRBC) are shown. The control for 100% hemolysis was a sample of erythrocytes treated with 0.1% Triton-X 100. The peptide concentration is in µM.
Figure 9A:
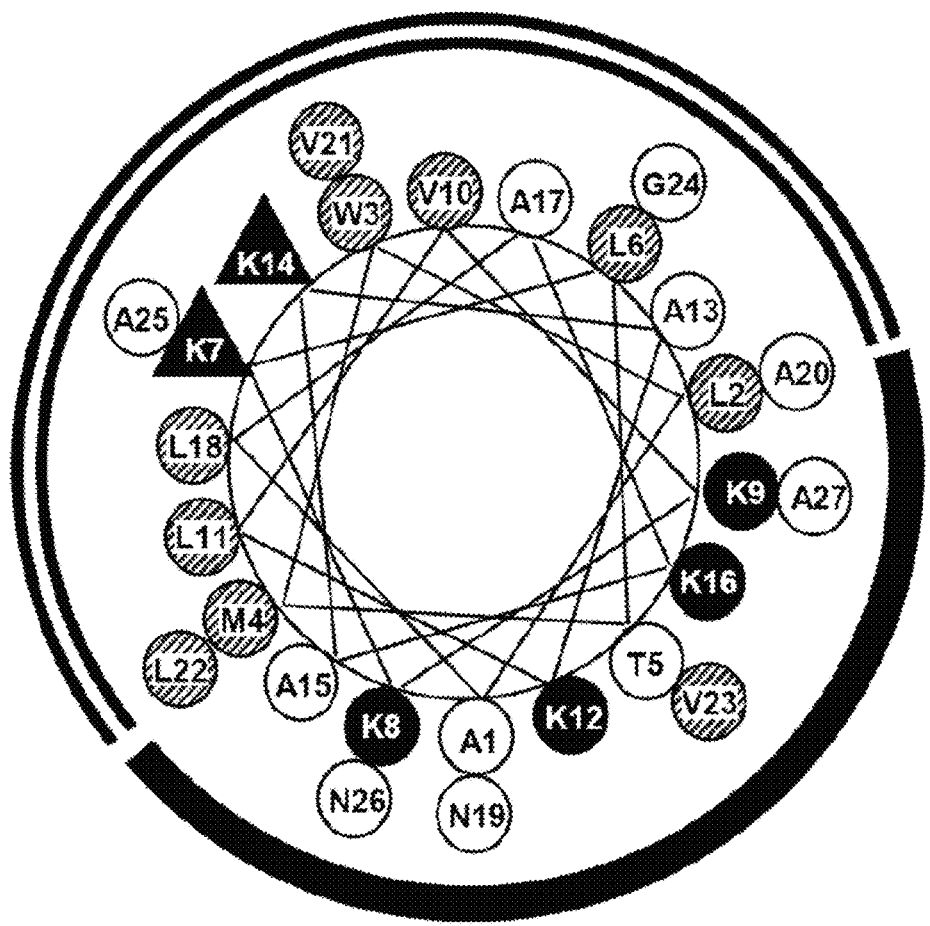
FIGS. 9A-9B illustrate structural configurations of the peptide D-Dermaseptin S4 L7K, A14K.
Figure 9B:
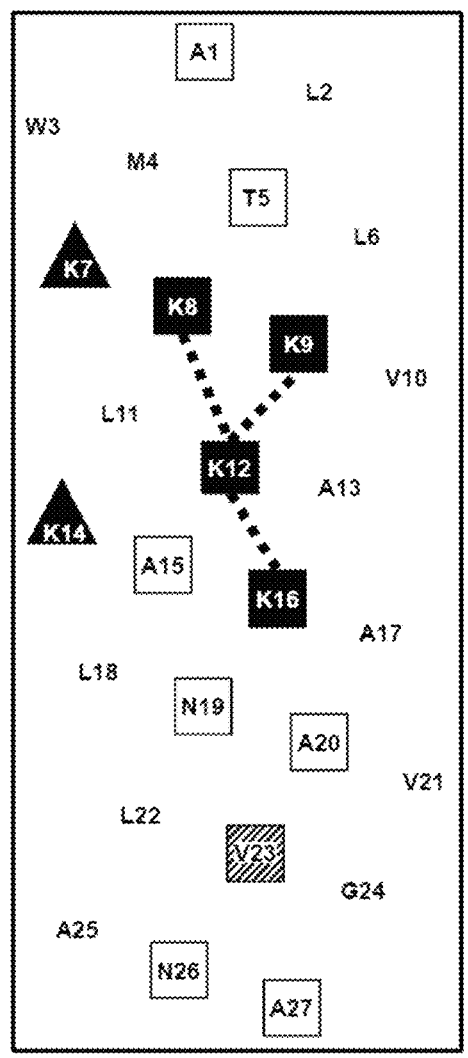
Figure 9B:
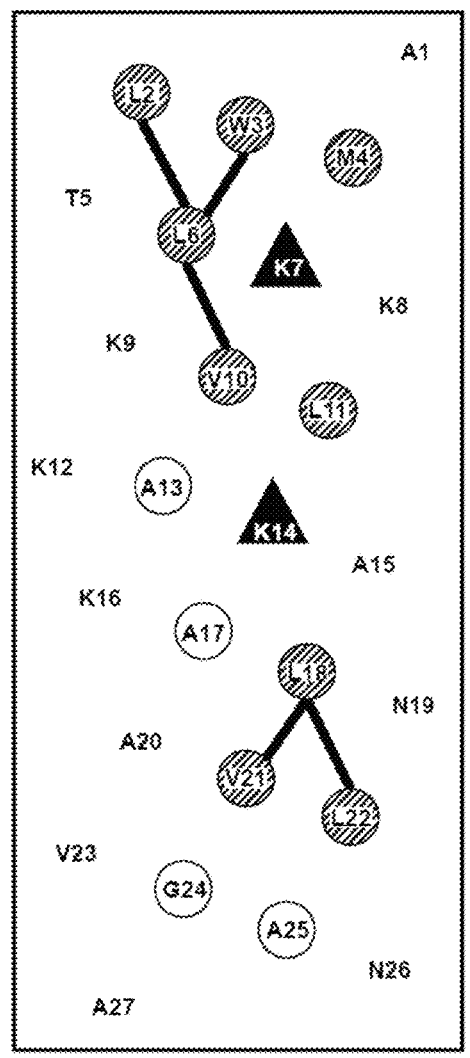

Hemolysis of human red blood cells is commonly used for in vitro assessment of AMP toxicity to normal cells. Many variations of this assay exist and inconsistency in red blood cells source, peptide exposure time and reporting of peptide concentrations impede comparison of AMP toxicity. The length of time erythrocytes are exposed to AMPs during the hemolysis assay is the least standardized parameter of the method, and the most commonly cited times are 30 min and 1 hour. However, higher exposure times are necessary to evaluate longer-term toxicity. For this reason, the inventors compared hemolytic activity at 1 hour and 18 hours for two D-Piscidin 1 analogs I9K, and G8P. As shown in FIG. 8, the $HC_{50}$ value increased dramatically from 1 hour to 18 hours. Thus, the hemolytic activity ($HC_{50}$) for the G8P analog at 1 hour incubation time at 37° C. was 55 μM; in contrast, at 18 hours at 37° C., the $HC_{50}$ was 8 μM (a 7-fold increase in hemolytic activity from 1 to 18 hours). Similarly, for D-Piscidin 119K, the hemolytic activity at 1000 μg/mL (387 μM) for 1 hour was only 32% hemolysis ($HC_{50}$ could not be determined) and at 18 hour incubation time the $HC_{50}$ was 115 μM. Based on these results, when determining hemolytic activity of antimicrobial peptides the concentration of same can be varied up to at least 1000 μg/mL in the assay. Also, an exposure/incubation time with human red blood cells can include a time of 18 hours. Under these conditions, $HC_{50}$ values can be accurately determined and will provide the best data for selecting analogs with low or no hemolytic activity. The inventors have observed that using 30 min or 1-hour exposure times and lower peptide concentrations can provide misleading data.

3.8. Therapeutic Index

The therapeutic indices are shown in Table 4. Large values indicate greater antimicrobial specificity. The substitution of Lys residues in the non-polar face maintained antimicrobial activity against six strains of *P. aeruginosa* and eleven strains of *A. baumannii* and dramatically decreased hemolytic activities against human red blood cells by 54-fold and 402-fold for D-Piscidin 119K and D-Dermaseptin S4 L7K, A14K, respectively. The geometric mean of the MIC values from eleven different diverse strains of *A. baumannii* was unchanged between native D-Piscidin 1 and D-Piscidin I9K, at 2.8 μM and 3.0 μM, respectively. The geometric mean of the MIC values from six different diverse strains of *P. aeruginosa* between native D-Piscidin 1 and D-Piscidin I9K increased from 19.3 μM and 30.5 μM. In the case of D-Dermaseptin S4, the geometric mean of MIC values for *A. baumannii* decreased from 1.8 μM for D-Dermaseptin S4 to 1.1 μM for D-Dermaseptin S4 L7K, A14K indicating a small improvement in antimicrobial activity. Similarly, with *P. aeruginosa*, the improvement in antimicrobial activity changed from a geometric mean of 12.6 μM for D-Dermaseptin S4 to 4.9 μM for D-Dermaseptin S4 L7K, A14K, representing a 2.5-fold improvement. D-Piscidin 1I9K, the most selective peptide among Piscidin 1 analogs, showed an increase in the therapeutic index from 0.1 for native D-Piscidin 1 to 3.2 for *P. aeruginosa*, a 32-fold improvement; while for *A. baumannii*, the therapeutic index increased from 0.6 for native D-Piscidin 1 to 33, a 55-fold improvement. D-Dermaseptin S4 L7K, A14K, the most selective peptide of Dermaseptin S4 analogs, showed a dramatically improved therapeutic index of 980-fold for *P. aeruginosa*, from 0.05 for native D-Dermaseptin S4 to 49 for this analog; for *A. baumannii*, the therapeutic index improved by 730-fold from 0.3 for native D-Dermaseptin S4 to 219 for this analog.

3.9. Mechanism of AMP Interaction with Membranes

Without wishing to be bound by any particular theory, the inventors have endeavored to understand the underlying mechanisms which may be relevant to the discoveries and advances the inventors have described. The above observations can be explained by the inventors' membrane discrimination mechanism. The inventors suggest that AMPs have activity against zwitterionic eukaryotic membranes by a pore-formation mechanism ("barrel-stave" mechanism); the peptides must be able to form a transmembrane pore. However the introduction of "specificity determinant(s)" prevents transmembrane penetration in the bilayer of eukaryotic cells. On the other hand, interaction of AMPs with negatively charged prokaryotic cell membranes utilizes the detergent-like mechanism ("carpet" mechanism) and transmembrane insertion is not required for antimicrobial activity. The peptides can lie parallel to the membrane surface where the positively charged residues on the polar face interact with the negatively charged phospholipid head groups of the bilayer and the ε-amino group of the Lys side-chain of the "specificity determinant(s)" may be long enough to avoid the hydrophobicity of the bilayer when lying parallel to the membrane surface even though they are on the non-polar face of the AMP. The peptides are still able to disrupt the lipid bilayer causing cytoplasmic leakage and cell death.

The differences in how Piscidin 1 interacts with the two membrane types (zwitterionic vs. negatively-charged) are understood in light of NMR structures, CD data and MD simulations. The results strongly demonstrate that the peptide inserts perpendicular to the POPC (1-palmitoyl-oleoyl-glycero-phosphocholine, neutral lipid) bilayer, whereas the peptide interacts only peripherally with the POPG (palmitoyl-oleoylphosphtidylglycerol, negatively-charged lipid) bilayer (a carpet-like manner). Furthermore, the hydrophobic residues largely interact with the zwitterionic membrane model while positively charged residues favorably interact with the negatively-charged membranes. The inventors' understanding is that not only does the cationic peptide preferentially interact with the negatively charged lipid molecules, but it may also cluster them; such peptide-lipid interactions are optimized at the bilayer interface, possibly as a prerequisite for bilayer disruption which allows Piscidin to initiate its disruptive behavior in the form of small aggregates. In conclusion, 1) zwitterionic and negatively-charged phospholipids did not have the same response against Piscidin 1 binding; 2) such differential interactions are related to the balance of electrostatic and hydrophobic interactions of Piscidin 1 with the zwitterionic vs. negatively-charged bilayer types.

4. Conclusions

The inventors have taken native AMPs, Piscidin 1 and Dermaseptin S4, and developed significantly active peptides. The inventors have expanded the "specificity determinant" design concept to effect a dramatic reduction in AMP toxicity (measured by hemolytic activity of human red blood cells). Substitution of a single lysine residue in the non-polar face of D-Piscidin 1 lowered the hemolytic activity by 54-fold from a $HC_{50}$ value of 1.8 µM to 98 µM for D-Piscidin 1 I9K. In the case of D-Dermaseptin S4, substitution of two lysine residues in the non-polar face lowered the hemolytic activity by 402-fold from a $HC_{50}$ value of 0.6 µM to 241 µM for D-Dermaseptin S4 L7K, A14K. Antimicrobial activity, as expressed by the geometric mean of 11 diverse strains of *A. baumannii*, was maintained for D-Piscidin 1 I9K and a small improvement was observed for D-Dermaseptin S4 L7K, A14K. Improvements in the therapeutic indices for these analogs were 55-fold (D-Piscidin 1 I9K) and 730-fold (D-Dermaseptin S4 L7K, A14K). Similarly, improvements in the therapeutic indices against 6 diverse strains of *P. aeruginosa* for these analogs were 32-fold and 980-fold, respectively. Comparison of the therapeutic indices of these two analogs (summarized in Table 4) showed that D-Dermaseptin S4 L7K, A14K, with a therapeutic index of 49 for *P. aeruginosa* and 219 for *A. baumannii*, has the desired properties for systemic use as a therapeutic against these two Gram-negative pathogens. In addition to the desired biological activity, D-Dermaseptin S4 L7K, A14K, has the desired biophysical properties. The two specificity determinants dramatically decreased helicity in aqueous medium, decreased overall hydrophobicity and hydrophobicity of the non-polar face, decreased amphipathicity and decreased self-association, all of which keeps the peptide as a random coil (which is a relatively unstructured state, or a state that can be referred to as no structure in comparison to other peptide structural motifs) in aqueous medium. This result supports the view of the underlying mechanism, where this structural feature (of random coil structure) facilitates easy passage of the unstructured peptide monomer through the capsule and cell wall to reach the cytoplasmic membrane, the target of the AMP. At the membrane surface, the peptide cannot form a transmembrane pore due to the presence of the positively-charged lysine residues on the non-polar face which prevents transmembrane burial in the bilayer. Thus, the AMP cannot enter the membrane of eukaryotic cells but can lie parallel to the membrane surface in the interface region of prokaryotic cells, where the hydrophobicity of the lipid bilayer induces the AMP into its α-helical structure and the AMP can disrupt the lipid bilayer by the carpet mechanism, causing leakage and cell death.

In the context of analysis of peptides, the inventors have shown that the use of short exposure time (1 hour) for determining hemolytic activity is not appropriate, and that an 18 hour exposure and peptide concentrations up to 1000 µg/mL are best for selecting analogs with improved therapeutic indices.

The development of useful and improved AMPs, including the generation of Piscidin-1 and Dermaseptin S4 derivatives and variants, especially such AMPs with improved properties, represents a significant advance.

Example 2

This Example provides further peptide variations of this disclosure. Additional modifications of Dermaseptin S4 peptides and modifications of Dermaseptin S4 L7K, A14K peptides are described. Examples of such modified peptides are shown in Table 5. Thus, derivatives and variants of the antimicrobial peptides of this disclosure can be substituted depicted in Table 5 to improve hydrophobicity on the non-polar face, improve hydrophilicity on the polar face, change amphipathicity or change location of specificity determinants.

TABLE 5

| Peptide name | Length | Sequence | SEQ ID NO. |
|---|---|---|---|
| D-Dermaseptin S4 L7K AL4K | 27 | NH₂-ALWMTL<u>K</u>KKVLKA<u>K</u>AKALNAVLVGANA-amide | 9 |
| D-Dermaseptin S4 (27 mer) | 27 | NH₂-ALWMTLLKKVLKAAAKALNAVLVGANA-amide | 6 |
| D-Dermaseptin S4 (28 mer) | 28 | NH₂-ALWMTLLKKVLKAAAKAALNAVLVGANA-amide | 11 |
| D-Dermaseptin S4 (28 mer) L7K, A14K | 28 | NH₂-ALWMTL<u>K</u>KKVLKA<u>K</u>AKAALNAVLVGANA-amide | 12 |
| Truncation | | | |
| D-Dermaseptin S4 L7K, A14K (1-16) | 16 | NH₂-ALWMTL<u>K</u>KKVLKA<u>K</u>AK-amide | 13 |

TABLE 5-continued

| Peptide name | Length | Sequence | SEQ ID NO. |
|---|---|---|---|
| *Different specificity determinant(s)* | | | |
| D-Dermaseptin S4 L6K, A14K | 27 | NH$_2$-ALWMT<u>K</u>LKKVLKA<u>K</u>AKALNAVLVGANA-amide | 14 |
| *V23 modification (change in amphipathicity)* | | | |
| D-Dermaseptin S4 L7K, A14K, V23S | 27 | NH$_2$-ALWMTL<u>K</u>KKVLKA<u>K</u>AKALNAVLSGANA-amide | 15 |
| D-Dermaseptin S4 L7K, A14K, V23K | 27 | NH$_2$-ALWMTL<u>K</u>KKVLKA<u>K</u>AKALNAVLKGANA-amide | 16 |
| D-Dermaseptin S4 L7K, A14K, A25V, V23A | 27 | NH$_2$-ALWMTL<u>K</u>KKVLKA<u>K</u>AKALNAVLAGVNA-amide | 17 |
| *Increased hydrophobicity* | | | |
| D-Dermaseptin S4 L7K, A14K, A17L | 27 | NH$_2$-ALWMTL<u>K</u>KKVLKA<u>K</u>AKLLNAVLVGANA-amide | 18 |
| D-Dermaseptin S4 L7K, A14K, A25L | 27 | NH$_2$-ALWMTL<u>K</u>KKVLKA<u>K</u>AKALNAVLVGLNA-amide | 19 |
| D-Dermaseptin S4 L7K, A14K, A17L, A25L | 27 | NH$_2$-ALWMTL<u>K</u>KKVLKA<u>K</u>AKLLNAVLVGLNA-amide | 20 |

Underline: specificity determinant(s).
Bold: other substitutions.
All peptide modifications are in the 27-residue peptide except where indicated.

Various peptides of the invention were tested for antimicrobial activity as described in Example 1. The antimicrobial activity of these peptides was similarly tested against Gram-positive organisms, including *Staphylococcus aureus*.

Table 6 shows the antimicrobial activity and pathogen selectivity factor of D-Piscidin 1 or D-dermaseptin S4 peptides, which indicates the loss of antimicrobial activity against *S. aureus* by 56 and 58 fold for D-Piscidin 1 V12K and D-Piscidin 1 I9K. and the maintenance of activity against *Acinetobacter baumannii* and *P. aeruginosa*. The loss of activity against *S. aureus* is indicative of gram-negative pathogen selectivity. The fold increase in selectivity for *Acinetobacter baumannii* over *S. aureus* is 56 and 55 fold and 64 fold and 37 for *P. aeruginosa* for D-Piscidin 1 V12K and D-Piscidin 119K, respectively. Similarly, for D-Dermaseptin S4 L7K, A14K the loss of antimicrobial activity against *S. aureus* was 61 fold and the pathogen selectivity factor for gram-negative pathogens was greater then 100-fold fox *Acinetobacter baumannii* and 156-fold for *P. aeruginosa*. In Table 6 peptides with a high fold increase in gram negative bacteria selectively are shown in bold.

Table 7 shows results of hemolytic activity of the tested peptides on human red blood cells (hRBC) following 18 hours incubation, including the fold decrease in hemolytic activity compared to the wild type D-Piscidin 1 or D-Dermaseptin S4 peptides (peptides with high fold increase—indicating substantial decrease in hemolytic activity against the organism tested—are shown in bold). The analogs D-Piscidin 119K and D-Dermaseptin S4 L7K, A14K are inactive against human red blood cells and *S. aureus* demonstrating eukaryotic cell selectivity and gram-negative pathogen selectivity. Table 7 also show s the selectivity of the tested peptides for eukaryotic cells (human red blood cells) or prokaryotic cells (Gram-positive or gram negative bacteria). Fold increase values for antimicrobial peptides showing a substantial selectivity for gram negative bacteria over eukaryotic cells are shows in bold. The selectivity factor for prokaryotic cells over eukaryotic cells in 54-fold for *Acinetobacter baumannii* and 36-fold for *P. aeruginosa* for D-Piscidin 119K, and 730-fold for *Acinetobacter baumannii* and 984-fold for *P. aruginosa* for D-dermaseptin S4 L7K, A14K.

Tables 8 and 9 show the antimicrobial activity of D-Piscidin 1 analogs and D-Dermaseptin S4 analogs against methicillin sensitive or resistant *S. aureus*, respectively. Similar antimicrobial activity against sensitive and resistant strains of *S. aureus* suggests the mechanism of action of AMPs is different from classical antibiotics and that AMPs are unaffected by antibiotic resistance.

TABLE 6

| | Antimicrobial activity (μM) | | | | | | Pathogen Selectivity Factor[c] | | | | | |
|---|---|---|---|---|---|---|---|---|---|---|---|---|
| | S. aureus | | A. baumannii | | P. aeruginosa | | S. aureus | | S. aureus | | P. aeruginosa | |
| Peptide Name | MIC$_{GM}$[a] | Fold[b] | MIC$_{GM}$[a] | Fold[b] | MIC$_{GM}$[a] | Fold[b] | A. baumannii | Fold[d] | P. aeruginosa | Fold[d] | A. baumannii | Fold[d] |
| D-Piscidin 1 | 3.1 | 1.0 | 2.8 | 1.0 | 19.3 | 1.0 | 1.1 | 1.0 | 0.16 | 1.0 | 6.9 | 1.0 |
| D-Piscidin 1 V12K | 173 | 56 | 2.8 | 1.0 | 17.0 | 1.1 | 62 | 56 | 10.2 | 64 | 6.1 | 1.1 |
| D-Piscidin 1 I9K | 180 | 58 | 3.0 | 1.1 | 30.5 | 1.6 | 60 | 55 | 5.9 | 37 | 10.2 | 1.5 |
| D-Dermaseptin S4 (27-mer) | 5.8 | 1.0 | 1.8 | 1.0 | 12.6 | 1.0 | 3.2 | 1.0 | 0.46 | 1.0 | 7.0 | 1.0 |
| D-Dermaseptin S4 L7K (27-mer) | 7.4 | 1.3 | 0.7 | 2.6 | 2.8 | 4.5 | 10.6 | 3.3 | 2.6 | 5.7 | 4.0 | 1.8 |

TABLE 6-continued

| | Antimicrobial activity (μM) | | | | | | Pathogen Selectivity Factor[c] | | | | | |
| --- | --- | --- | --- | --- | --- | --- | --- | --- | --- | --- | --- | --- |
| | S. aureus | | A.baumannii | | P. aeruginosa | | S. aureus | | S. aureus | | P. aeruginosa | |
| Peptide Name | MIC$_{GM}$[a] | Fold[b] | MIC$_{GM}$[a] | Fold[b] | MIC$_{GM}$[a] | Fold[b] | A.baumannii | Fold[d] | P. aeruginosa | Fold[d] | A. baumannii | Fold[d] |
| D-Dermaseptin S4 L7K,A14K (27-mer) | >351 | 61 | 1.1 | 1.6 | 4.9 | 2.6 | >319 | >100 | >71.6 | >156 | 4.5 | 1.6 |

[a]MIC is the minimum inhibitory concentration (μM) of peptide that inhibits growth of bacteria after 24 hours at 37° C. MIC$_{GM}$ is the geometric mean of the MIC values from 20 different isolates of S. aureus, 11 different isolates of A. batanannii or 6 different isolates of P. aeruginosa.
[b]Fold change in antimicrobial activity compared to native D-Piscidin 1 or native D-Derm.aseptin S4. The values with a large fold change are bolded.
[c]Selectivity factor is the ratio of MIC$_{GM}$ (μM) for two different organisms.
dFold change in selectivity factor compared to native D-Piscidin 1 or native D-Dermaseptin S4. The values with a large fold change are bolded.

TABLE 7

| | Hemolytic Activity | | | | Eukaryotic/ Prokaryotic Cell Selectivity Factor | | | | | | |
| --- | --- | --- | --- | --- | --- | --- | --- | --- | --- | --- | --- |
| Peptide Name | HC$_{50}$[a] (μM) | Fold[b] | MIC$_{GM}$ (Sa) (μM) | hRBC/ S. aureus | Fold[d] | MIC$_{GM}$ (Ab) (μM) | hRBC/ A. baumannii | Fold[d] | MIC$_{GM}$ (Pa) (μM) | hRBC/ P. aeruginosa | Fold[d] |
| D-Piscidin 1 | 1.8 | 1.0 | 3.1 | 0.6 | 1.0 | 2.8 | 0.6 | 1.0 | 19.3 | 0.09 | 1.0 |
| D-Piscidin 1 V12K | 35 | 19 | 173.3 | 0.2 | 3.0 | 2.8 | 12.5 | 21.0 | 17.0 | 2.1 | 23 |
| D-Piscidin 1 I9K | 98 | 54 | 180.4 | 0.5 | 1.2 | 3.0 | 32.6 | 54 | 30.5 | 32 | 36 |
| D-Dermaseptin S4 (7-mer) | 0.6 | 1.0 | 5.8 | 0.1 | 1.0 | 1.8 | 0.3 | 1.0 | 12.6 | 0.05 | 1.0 |
| D-Dermaseptin S4 L7K | 8.6 | 14 | 7.4 | 1.2 | 12 | 0.7 | 12.3 | 41 | 2.8 | 3.1 | 62 |
| D-Dermaseptin S4 L7K,A14K | 241 | 402 | >350.8 | <0.7 | 7.0 | 1.1 | 219 | 730 | 4.9 | 49 | 984 |

[a]HC$_{50}$ is the concentration of peptide (μM) that results in 50% hemolysis after 18 hours at 37° C. The best HC$_{50}$ values are bolded.
[b]Fold improvement in HC$_{50}$ compared to that of D-Piscidin 1 or D-Dermaseptin S4. The best values for fold improvement are bolded.
[c]Selectivity factor is the ratio of HC$_{50}$ value for human red blood cells (UM) over the geometric mean MIC value (μM).
[d]Fold change in selectivity factor compared to native D-Piscidin 1 or D-Dermaseptin S4.

TABLE 8

Antimicrobial activity against methicillin sensitive Staph. aureus (MSSA)

| | MIC[a] (μM) Strain | | | | | | |
| --- | --- | --- | --- | --- | --- | --- | --- |
| | M22315 | M22274 | M22300 | M22287 | M22312 | M21935 | M22111 |
| | | | | Source | | | |
| Peptide | Spine | Finger | Hip | Finger | Resp | | Ear |
| D-Piscidin 1 | 3.0 | 3.0 | 3.0 | 3.0 | 6.1 | 3.0 | 1.5 |
| D-Piscidin 1 V12K | 192 | 769 | 24.0 | 192 | 769 | 192 | 6.0 |
| D-Piscidin 1 I9K | 773 | 773 | 773 | 773 | 773 | 387 | 3.0 |
| D-Dermaseptin S4 (27-mer) | 11.3 | 11.3 | 5.6 | 5.6 | 11.3 | 5.6 | 5.6 |
| D-Dermaseptin S4L7K (27-mer) | 11.2 | 22.4 | 11.2 | 11.2 | 5.6 | 2.8 | 5.6 |
| D-Dermaseptin S4 L7K,A14K (27-mer) | >351 | >351 | >351 | >351 | >351 | >351 | 87.7 |

| | MIC[a] (μM) Strain | | | | | | |
| --- | --- | --- | --- | --- | --- | --- | --- |
| | M22075 | M21913 | BL7429 | M22097 | M21991 | | |
| | | | | Source | | | |
| Peptide | Axilla | Finger | Blood | Neck | Resp. | GM[b] | Fold[c] |
| D- Piscidin 1 | 3.0 | 3.0 | 3.0 | 6.1 | 6.1 | 3.4 | 1.0 |
| D-Piscidin 1 V12K | 385 | 769 | 385 | 385 | 769 | 229 | 67 |
| D-Piscidin 1 I9K | 387 | 193 | 193 | 193 | 273 | 80 | |
| D-Dermaseptin S4 (27-mer) | 2.8 | 5.6 | 2.8 | 5.6 | 5.6 | 6.0 | 1.0 |
| D-Dermaseptin S4 L7K (27-mer) | 11.2 | 5.6 | 11.2 | 5.6 | 8.4 | 1.4 | |

TABLE 8-continued

Antimicrobial activity against methicillin sensitive Staph. aureus (MSSA)

| | | | | | | | |
|---|---|---|---|---|---|---|---|
| D-Dermaseptin S4 L7K,A14K (27-mer) | >351 | >351 | >351 | >351 | >351 | >351 | >58 |

<sup>a</sup>MIC is minimal inhibitory concentration (μM) that inhibited growth of different strains in Mueller-Hinton (MH) medium at 37° C. after 24h MIC is given based on three sets of determinations.
<sup>b</sup>GM is the geometric mean of the MIC values from 12 different isolates of MSSA (A) and 8 different isolates of MRSA (B).
<sup>c</sup>The fold loss in antimicrobial activity (geometric mean data) against S. aureus compared to that of native D-Piscidin 1 or D-Dermaseptin S4.

TABLE 9

Antimicrobial activity against methicillin resistant Staph. aureus (MRSA)

| | MICa (μM) | | | | | | | | |
|---|---|---|---|---|---|---|---|---|---|
| | Strain | | | | | | | | |
| | M22424 | M22111 | M22360 | M22354 | M21756 | M22130 | M22224 | M21742 | |
| | Source | | | | | | | | |
| Peptide | Arm | Ear | Labia | Nose | | Leg | Nose | GM[b] | Fold[c] |
| D-Piscidin 1 | 3.0 | 3.0 | 1.5 | 3.0 | 3.0 | 3.0 | 3.0 | 3.0 | 2.8 | 1.0 |
| D-Piscidin 1 V12K | 769 | 96.1 | 3.0 | 96.1 | 385 | 96.1 | 96.1 | 385 | 114 | 41 |
| D-Piscidin 1 I9K | 773 | 96.7 | 3.0 | 773 | 387 | 12.1 | 96.7 | 96.7 | 96.7 | 35 |
| D-Dermaseptin S4 (27-mer) | 11.3 | 5.6 | 5.6 | 5.6 | 2.8 | 5.6 | 5.6 | 5.6 | 5.6 | 1.0 |
| D-Dermaseptin S4 L7K(2-mer) | 11.2 | 11.2 | 2.8 | 5.6 | 5.6 | 5.6 | 5.6 | 5.6 | 6.1 | 1.1 |
| D-Dermaseptin S4 L7K,A14K (27-mer) | >351 | >351 | >351 | >351 | >351 | >351 | >351 | >351 | >351 | >63 |

<sup>a</sup>MIC is minimal inhibitory concentration (μM) that inhibited growth of different strains in Mueller-Hinton (MH) medium at 37° C. after 24h. WC is given based on three sets of determinations.
<sup>b</sup>GM is the geometric mean of the MIC values from 12 different isolates of MSSA (A) and 8 different isolates of MRSA (B).
<sup>c</sup>The fold loss in antimicrobial activity (geometric mean data) against S. aureus compared to that of native D-Piscidin 1 or D-Dermaseptin S4.

REFERENCES

1. World Health Organization *The use of essential drugs. Sixth report of the WHO Expert Committee Geneva*, WHO Technical Report Series, No. 850; 1995.
2. U. S. Congress *Impacts of antibiotic-resistant bacteria. Office of Technology Assessment*; Washington, D.C., 1995.
3. House of Lords, U. K. *Science and technology 7th report; resistance to antibiotics and other antimicrobial agents*; House of Lords, London, United Kingdom: 1998: pp HL Paper 81-11, session 1997-1998.
4. Garza-Gonzalez, E.; Llaca-Diaz, J. M.; Bosques-Padilla, F. J.; Gonzalez, G. M. Prevalence of multidrug-resistant bacteria at a tertiary-care teaching hospital in Mexico: special focus on *Acinetobacter baumannii*. *Chemotherapy* 2010, 56, 275-279.
5. Bland, J. M.; De Lucca, A. J.; Jacks, T. J.; Vigo, C. B. All-D-cecropin B: synthesis, conformation, lipopolysaccharide binding, and antibacterial activity. *Molecular and cellular biochemistry* 2001, 218, 105-111.
6. Cribbs, D. H.; Pike, C. J.; Weinstein, S. L.; Velazquez, P.; Cotman, C. W. All-D-enantiomers of beta-amyloid exhibit similar biological properties to all-L-beta-amyloids. *The Journal of biological chemistry* 1997, 272, 7431-7436.
7. De Lucca. A. J.; Bland, J. M.; Vigo, C. B.; Jacks, T. J.; Peter, J.; Walsh, T. J. D-cecropin B: proteolytic resistance, lethality for pathogenic fungi and binding properties. *Med Mycol* 2000, 38, 301-308.
8. Elmquist, A.; Langel, U. In vitro uptake and stability study of pVEC and its all-D analog. *Biological chemistry* 2003, 384, 387-393.
9. Hamamoto, K.; Kida, Y.; Zhang, Y.; Shimizu, T.; Kuwano, K. Antimicrobial activity and stability to proteolysis of small linear cationic peptides with D-amino acid substitutions. *Microbiology and immunology* 2002, 46, 741-749.
10. Hong, S. Y.; Oh. J. E.; Lee, K. H. Effect of D-amino acid substitution on the stability, the secondary structure, and the activity of membrane-active peptide. *Biochemical pharmacology* 1999, 58, 1775-1780.
11. Wade, D.; Boman, A.; Wahlin, B.; Drain, C. M.; Andreu, D.; Boman, H. G.; Merrifield. R. B. All-D amino acid-containing channel-forming antibiotic peptides. *Proceedings of the National Academy of Sciences of the United States of America* 1990, 87, 4761-4765.
12. Wakabayashi, H.; Matsumoto, H.; Hashimoto, K.; Teraguchi, S.; Takase, M.; Hayasawa, H. N-Acylated and D enantiomer derivatives of a nonamer core peptide of lactoferricin B showing improved antimicrobial activity. *Antimicrobial agents and chemotherapy* 1999, 43, 1267-1269.
13. Chen, Y.; Vasil, A. I.; Rehaume, L.; Mant, C. T.; Burns, J. L.; Vasil, M. L.; Hancock, R. E.; Hodges, R. S. Comparison of biophy sical and biologic properties of alpha-helical enantiomeric antimicrobial peptides. *Chemical biology &drug design* 2006, 67, 162-173.
14. Gura, T. Innate immunity. Ancient system gets new respect. *Science* (New York, N.Y. 2001, 291, 2068-2071.
15. Levy, O. Antimicrobial proteins and peptides of blood, templates for novel antimicrobial agents. *Blood* 2000, 96, 2664-2672.
16. Chen, Y.; Mant, C. T.; Farmer, S. W.; Hancock, R. E.; Vasil, M. L.; Hodges, R. S. Rational design of alpha- 17. Jiang, Z.; Vasil, A. I.; Gera, L.; Vasil, M. L.; Hodges, R. S. Rational design of alpha-helical antimicrobial peptides to target Gram-negative pathogens, *Acinetobacter baumannii* and *Pseudomonas aeruginosa*; utilization of charge, 'specificity determinants,' total hydrophobicity, hydrophobe type and location as design parameters to improve the therapeutic ratio. *Chemical biology &drug design* 2011, 77, 225-240.

18. Mor, A.; Nguyen Van, H.; Delfour, A.; Migliore-Samour, D.; Nicolas, P. Isolation, amino acid sequence and synthesis of dermaseptin, a novel antimicrobial peptide of amphibian skin. *Biochemistry* 1991, 30, 8824-8830.

19. Mor, A.; Amiche, M.; Nicolas, P. Structure, synthesis, and activity of Dermaseptin b, a novel vertebrate defensive peptide from frog skin, relationship with adenoregulin. *Biochemistry* 1994, 33, 6642-6650.

20. Mor, A.; Hani, K.; Nicolas, P. The vertebrate peptide antibiotics dermaseptins have overlapping structural features but target specific microorganisms. *The Journal of biological chemistry* 1994, 269, 31635-31641.

21. Belaid, A.; Aouni, M.; Khelifa, R.; Trabelsi, A.; Jemmali, M.; Hani, K. In vitro antiviral activity of dermaseptins against herpes simplex virus type 1. *Journal of medical virology* 2002, 66, 229-234.

22. Lorin, C.; Saidi, H.; Belaid, A.; Zairi, A.; Baleux, F.; Hocini, H.; Belec, L.; Hani, K.; Tangy, F. The antimicrobial peptide dermaseptin S4 inhibits HIV-1 infectivity in vitro. *Virology* 2005, 334, 264-275.

23. Feder, R.; Dagan, A.; Mor, A. Structure-activity relationship study of antimicrobial dermaseptin S4 showing the consequences of peptide oligomerization on selective cytotoxicity. *The Journal of biological chemistry* 2000, 27J, 4230-4238.

24. Navon-Venezia, S.; Feder, R.; Gaidukov, L.; Carmeli, Y.; Mor, A. Antibacterial properties of dermaseptin S4 derivatives with in vivo activity. *Antimicrobial agents and chemotherapy* 2002, 46, 689-694.

25. Feder, R.; Nehushtai, R.; Mor, A. Affinity driven molecular transfer from erythrocyte membrane to target cells. *Peptides* 2001, 22, 1683-1690.

26. Kustanovich, I.; Shalev, D. E.; Mikhlin, M.; Gaidukov, L.; Mor, A. Structural requirements for potent versus selective cytotoxicity for antimicrobial dermaseptin S4 derivatives. *The Journal of biological chemistry* 2002, 277, 16941-16951.

27. Noga, E. J.; Silphaduang. U.; Park, N. G.; Seo, J. K.; Stephenson, J.; Kozlowicz. S. Piscidin 4, a novel member of the piscidin family of antimicrobial peptides. *Comparative biochemistry and physiology* 2009, 152, 299-305.

28. Silphaduang. U.; Noga. E. J. Antimicrobials: Peptide antibiotics in mast cells of fish. *Nature* 2001, 414, 268-269.

29. Noga, E. J.; Fan, Z.; Silphaduang. U. Histone-like proteins from fish are lethal to the parasitic dinoflagellate *Amyloodinium ocellatum*. *Parasitology* 2001, 123, 57-65.

30. Noga, E. J.; Silphaduang, U. Piscidins: a novel family of peptide antibiotics from fish. *Drug news & perspectives* 2003, 16, 87-92.

31. Lauth, X.; Shike, H.; Burns, J. C.; Westerman, M. E.; Ostland, V. E.; Carlberg, J. M.; Van Olst, J. C.; Nizet. V.; Taylor, S. W.; Shimizu, C.; Bulet, P. Discovery and characterization of two isoforms of moronecidin, a novel antimicrobial peptide from hybrid striped bass. *The Journal of biological chemistry* 2002, 277, 5030-5039.

32. Chinchar, V. G.; Bryan, L.; Silphadaung, U.; Noga, E.; Wade, D.; Rollins-Smith, L. Inactivation of viruses infecting ectothermic animals by amphibian and piscine antimicrobial peptides. *Virology* 2004, 323, 268-275.

33. Lee, S. A.; Kim, Y. K.; Lim, S. S.; Zhu, W. L.; Ko, H.; Shin, S. Y.; Hahm, K. S.; Kim, Y. Solution structure and cell selectivity of piscidin 1 and its analogues. *Biochemistry* 2007, 46, 3653-3663.

34. Menousek, J.; Mishra, B.; Hanke, M. L.; Heim, C. E.; Kielian, T.; Wang, G. Database screening and in vivo efficacy of antimicrobial peptides against methicillin-resistant *Staphylococcus aureus* USA300. *International journal of antimicrobial agents* 2012, 39, 402-406.

35. Chen, Y.; Mant, C. T.; Hodges, R. S. Preparative reversed-phase high-performance liquid chromatography collection efficiency for an antimicrobial peptide on columns of varying diameters (1 mm to 9.4 mm ID.). *Journal of chromatography* 2007, 1140, 112-120.

36. Lee, D. L.; Mant, C. T.; Hodges, R. S. A novel method to measure self-association of small amphipathic molecules, temperature profiling in reversed-phase chromatography. *The Journal of biological chemistry* 2003, 278, 22918-22927.

37. Chen, Y.; Guarnieri, M. T.; Vasil, A. I.; Vasil, M. L.; Mant, C. T.; Hodges, R. S. Role of peptide hydrophobicity in the mechanism of action of alpha-helical antimicrobial peptides. *Antimicrobial agents and chemotherapy* 2007, 51, 1398-1406.

38. Jiang, Z.; Hggins, M. P.; Whitehurst, J.; Kisich, K. O.; Voskuil, M. I.; Hodges, R. S. Anti-tuberculosis activity of alpha-helical antimicrobial peptides: de novo designed L- and D-enantiomers versus L- and D-LL-37. *Protein and peptide letters* 2010.

39. Jiang, Z.; Kullberg, B. J.; van der Lee, H.; Vasil, A. I.; Hale, J. D.; Mant, C. T.; Hancock, R. E. W.; Vasil, M. L.; Netea, M. G.; Hodges, R. S. Effects of Hydrophobicity on the Antifungal Activity of a-Helical Antimicrobial Peptides. *Chemical biology &drug design* 2008, 72, 483-495.

40. Jiang, Z.; Vasil, A I.; Hale, J. D.; Hancock, R. E.; Vasil, M. L.; Hodges, R. S. Effects of net charge and the number of positively charged residues on the biological activity of amphipathic alpha-helical cationic antimicrobial peptides. *Biopolymers* 2008, 90, 369-383.

41. Eisenberg, D.; Weiss, R. M.; Terwilliger, T. C. The helical hydrophobic moment: a measure of the amphiphilicity of a helix. *Nature* 1982, 299, 371-374.

42. Carver, T.; Bleasby, A. The design of Jemboss: a graphical user interface to EMBOSS. *Bioinformatics (Oxford, England)* 2003, 19, 1837-1843.

43. Kovacs, J. M.; Mant, C. T.; Hodges, R. S. Determination of intrinsic hydrophilicity/hydrophobicity of amino acid side chains in peptides in the absence of nearest-neighbor or conformational effects. *Biopolymers* 2006, 84, 283-297.

44. Mant, C. T.; Kovacs, J. M.; Kim, H. M.; Pollock, D. D.; Hodges, R. S. Intrinsic amino acid side-chain hydrophilicity/hydrophobicity coefficients determined by reversed-phase high-performance liquid chromatography of model peptides, comparison with other hydrophilicity/hydrophobicity scales. *Biopolymers* 2009, 92, 573-595.

45. Holloway, B. W. Genetic recombination in *Pseudomonas aeruginosa*. *Journal of general microbiology* 1955, 13, 572-581.

46. Bjorn, M. J.; Vasil, M. L.; Sadoff, J. C.; Iglewski, B. H. Incidence of exotoxin production by *Pseudomonas* species. *Infection and immunity* 1977, 16, 362-366.
47. Pavlovskis, O. R.; Pollack, M.; Callahan, L. T., 3rd; Iglewski, B. H. Passive protection by antitoxin in experimental *Pseudomonas aeruginosa* burn infections. *Infection and immunity* 1977, 18, 596-602.
48. Frost, L. S.; Paranchych, W. Composition and molecular w eight of pili purified from *Pseudomonas aeruginosa* K. *Journal of bacteriology* 1977, 131, 259-269.
49. Watts, T. H.; Kay, C. M.; Paranchych, W. Dissociation and characterization of pilin isolated from *Pseudomonas aeruginosa* strains PAK and PAO. *Canadian journal of biochemistry* 1982, 60, 867-872.
50. Rahme, L. G.; Ausubel, F. M.; Cao, H.; Drenkard, E.; Goumnerov, B. C.; Lau, G. W.; Mahajan-Miklos. S.; Plotnikova, J.; Tan, M. W.; Tsongalis, J.; Walendziewicz, C. L; Tompkins, R. G. Plants and animals share functionally common bacterial virulence factors. *Proceedings of the National Academy of Sciences of the United States of America* 2000, 97, 8815-8821.
51. Stieritz, D. D.; Holder, I. A. Experimental studies of the pathogenesis of infections due to *Pseudomonas aeruginosa*: description of a burned mouse model. *The Journal of infectious diseases* 1975, 131, 688-691.
52. Hawrani, A.; Howe, R. A.; Walsh, T. R.; Dempsey, C. E. Origin of low mammalian cell toxicity in a class of highly active antimicrobial amphipathic helical peptides. *The Journal of biological chemistry* 2008, 283, 18636-18645.
53. Shalev, D. E.; Rotem, S.; Fish, A.; Mor, A. Consequences of N-acylation on structure and membrane binding properties of dermaseptin derivative K4-S4-(1-13). *The Journal of biological chemistry* 2006, 281, 9432-9438.
54. Mant, C. T.; Chen, Y.; Hodges, R. S. Temperature profiling of polypeptides in reversed-phase liquid chromatography. I. Monitoring of dimerization and unfolding of amphipathic alpha-helical peptides. *Journal of chromatography* 2003, 1009, 29-43.
55. Mant, C. T.; Tripet, B.; Hodges, R. S. Temperature profiling of polypeptides in reversed-phase liquid chromatography. II. Monitoring of folding and stability of two-stranded alpha-helical coiled-coils. *Journal of chromatography* 2003, 1009, 45-59.
56. Ghosh, J. KL; Shaool. D.; Guillaud, P.; Ciceron, L.; Mazier, D.; Kustanovich, I.; Shai, Y.; Mor, A. Selective cytotoxicity of dermaseptin S3 toward intraerythrocytic *Plasmodium falciparum* and the underlying molecular basis. *The Journal of biological chemistry* 1997, 272, 31609-31616.
57. Hodges, R. S.; Jiang, Z.; Whitehurst, J.; Mant. C. T., Development of antimicrobial peptides as therapeutic agents. In *Development of Therapeutic Agents, Handbook in Pharmaceutical Sciences* Shayne Gad and Managing Editor (Editor-in-Chief, Michael Eventhal), Ed. John Wiley and Sons, 2012; pp. 285-357.
58. Blazyk, J.; Wiegand, R.; Klein, J.; Hammer, J.; Epand, R. M.; Epand, R. F.; Maloy, W. L.; Kari, U. P. A novel linear amphipathic beta-sheet cationic antimicrobial peptide with enhanced selectivity for bacterial lipids. *The Journal of biological chemistry* 2001, 276, 27899-27906.
59. Chekmenev, E. Y.; Vollmar, B. S.; Forseth, K. T.; Manion, M. N.; Jones, S. M.; Wagner. T. J.; Endicott, R. M.; Kyriss, B. P.; Homem, L. M.; Pate, M.; He, J.; Raines, J.; Gor'kov, P. L.; Brey, W. W.; Mitchell, D. J.; Auman, A. J.; Ellard-Ivey, M. J.; Blazyk, J.; Gotten, M. Investigating molecular recognition and biological function at interfaces using piscidins, antimicrobial peptides from fish. *Biochimica et biophysica acta* 2006, 1758, 1359-1372.
60. Gibson, B. W.; Tang, D. Z.; Mandrell, R.; Kelly, M.; Spindel, E. R. Bombinin-like peptides with antimicrobial activity from skin secretions of the Asian toad, *Bombina orientalis*. *The Journal of biological chemistry* 1991, 266, 23103-23111.
61. Coni on, J. M.; Sonnevend. A.; Davidson, C.; Smith. D. D.; Nielsen, P. F. The ascaphins: a family of antimicrobial peptides from the skin secretions of the most primitive extant frog, *Ascaphus truei*. *Biochemical and biophysical research communications* 2004, 320, 170-175.
62. Shin, S. Y.; Hahm. K. S. A short alpha-helical antimicrobial peptide with antibacterial selectivity. *Biotechnology letters* 2004, 26, 735-739.
63. Tencza, S. B.; Douglass, J. P.; Creighton, D. J., Jr.; Montelaro, R. C.; Mietzner, T. A. Novel antimicrobial peptides derived from human immunodeficiency virus type 1 and other lentivirus transmembrane proteins. *Antimicrobial agents and chemotherapy* 1997, 41, 2394-2398.
64. Baumann, G.; Mueller, P. A molecular model of membrane excitability. *Journal of supramolecular structure* 1974, 2, 538-557.
65. Ehrenstein, G.; Lecar, H. Electrically gated ionic channels in lipid bilayers. *Quarterly reviews of biophysics* 1977,10, 1-34.
66. Pouny, Y.; Rapaport, D.; Mor, A.; Nicolas, P.; Shai, Y. Interaction of antimicrobial dermaseptin and its fluorescently labeled analogues with phospholipid membranes. *Biochemistry* 1992, 31, 12416-12423.
67. Rahmanpour, A.; Ghahremanpour, M. M.; Mehmejad, F.; Moghaddam, M. E. Interaction of Piscidin-1 with zwitterionic versus anionic membranes: a comparative molecular dynamics study. *Journal of biomolecular structure &dynamics* 2012.
68. De Angelis, A. A; Grant, C. V.; Baxter, M. K.; McGavin, J. A.; Opella, S. J.; Gotten, M. L. Amphipathic antimicrobial piscidin in magnetically aligned lipid bilayers. *Biophysical journal* 2011, 101, 1086-1094.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

When a group of substituents is disclosed herein, it is understood that all individual members of that group and all subgroups, including any isomers, enantiomers, and diastereomers of the group members, are disclosed separately.

When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomer and enantiomer of the compound described individual or in any combination. Additionally, unless otherwise specified, all isotopic variants of compounds disclosed herein are intended to be encompassed by the disclosure. As a brief illustration, it will be understood that any one or more hydrogens in a molecule disclosed can be replaced with deuterium or tritium.

Isotopic variants of a molecule are generally useful as standards in assays for the molecule and in chemical and biological research related to the molecule or its use. Methods for making such isotopic variants are known in the art.

One of ordinary skill in the art will appreciate that starting materials, biological and chemical materials, biological and chemical reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this disclosure.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by various embodiments which may include preferred embodiments, exemplary embodiments and optional features, modifications and variations of the concepts herein disclosed may be resorted to by those skilled in the art. Such modifications and variations are considered to be within the scope of this invention as defined by the appended claims.

What is claimed is:

1. An antimicrobial peptide (AMP) comprising the amino acid sequence selected from the group consisting of: ALWMTLKKKVLKAKAKALNAVLKGANA (SEQ ID NO: 16); ALWMTLKKKVLKAKAKALNAVLAGVNA (SEQ ID NO: 17); and ALWMTLKKKVLKAKAKALNAVLVGLNA (SEQ ID NO: 19) or a pharmaceutically-acceptable salt thereof.

2. The AMP of claim 1, wherein the amino acid sequence of the AMP comprises the sequence of SEQ ID NO: 16.

3. The AMP of claim 1, wherein the amino acid sequence of the AMP comprises the sequence of SEQ ID NO: 17.

4. The AMP of claim 1, wherein the amino acid sequence of the AMP consists of the sequence of SEQ ID NO: 19.

5. The AMP of claim 1, wherein the AMP inhibits propagation of a Gram-negative bacterium.

6. The AMP of claim 5, wherein the Gram-negative bacterium is at least one of *A. baumannii* and *P. aeruginosa*.

7. A pharmaceutical composition comprising at least one peptide of claim 1 and a pharmaceutically acceptable carrier.

8. The pharmaceutical composition of claim 7, comprising a mono-phasic pharmaceutical composition suitable for parenteral or oral administration consisting essentially of a therapeutically-effective amount of at least one peptide of claim 1, and a pharmaceutically acceptable carrier.

9. A method of treating a Gram-negative bacterial infection comprising administering to a subject in need thereof a therapeutically effective amount of at least one peptide of claim 1 or a pharmaceutical composition of claim 7.

10. The method of claim 9, wherein the Gram-negative bacterial infection is an antibiotic resistant bacterial infection.

11. The method of claim 9, wherein an infecting microorganism is at least one of *Acinetobacter baumannii* and *Pseudomonas aeruginosa*.

12. The method of claim 9, wherein an infecting microorganism is multi-drug resistant *Pseudomonas aeruginosa* or *Acinetobacter baumannii*.

13. The method of claim 9, wherein the administration of the peptide or pharmaceutical composition is by an administration route selected from oral, topical, intravenous, intraperitoneal, intramuscular, intradermal, intrasternal, intraarticular injection, or infusion.

* * * * *

```
                          SEQUENCE LISTING

<160> NUMBER OF SEQ ID NOS: 20

<210> SEQ ID NO 1
<211> LENGTH: 22
<212> TYPE: PRT
<213> ORGANISM: Morone chrysops x Morone saxatilis

<400> SEQUENCE: 1

Phe Phe His His Ile Phe Arg Gly Ile Val His Val Gly Lys Thr Ile
1               5                   10                  15

His Arg Leu Val Thr Gly
            20

<210> SEQ ID NO 2
<211> LENGTH: 22
<212> TYPE: PRT
<213> ORGANISM: Artificial Sequence
<220> FEATURE:
<223> OTHER INFORMATION: synthetic peptide

<400> SEQUENCE: 2

Phe Phe His His Ile Phe Arg Pro Ile Val His Val Gly Lys Thr Ile
1               5                   10                  15

His Arg Leu Val Thr Gly
            20

<210> SEQ ID NO 3
<211> LENGTH: 22
<212> TYPE: PRT
<213> ORGANISM: Artificial Sequence
<220> FEATURE:
<223> OTHER INFORMATION: synthetic peptide

<400> SEQUENCE: 3

Phe Phe His His Ile Phe Arg Gly Lys Val His Val Gly Lys Thr Ile
1               5                   10                  15

His Arg Leu Val Thr Gly
            20

<210> SEQ ID NO 4
<211> LENGTH: 22
<212> TYPE: PRT
<213> ORGANISM: Artificial Sequence
<220> FEATURE:
<223> OTHER INFORMATION: synthetic peptide

<400> SEQUENCE: 4
```

```
Phe Phe His His Ile Phe Arg Gly Ile Val His Lys Gly Lys Thr Ile
1               5                   10                  15

His Arg Leu Val Thr Gly
            20
```

<210> SEQ ID NO 5
<211> LENGTH: 22
<212> TYPE: PRT
<213> ORGANISM: Artificial Sequence
<220> FEATURE:
<223> OTHER INFORMATION: synthetic peptide

<400> SEQUENCE: 5

```
Phe Phe His His Ile Phe Arg Gly Ile Val His Val Lys Lys Thr Ile
1               5                   10                  15

His Arg Leu Val Thr Gly
            20
```

<210> SEQ ID NO 6
<211> LENGTH: 27
<212> TYPE: PRT
<213> ORGANISM: Phyllomedusa sauvagei

<400> SEQUENCE: 6

```
Ala Leu Trp Met Thr Leu Leu Lys Lys Val Leu Lys Ala Ala Ala Lys
1               5                   10                  15

Ala Leu Asn Ala Val Leu Val Gly Ala Asn Ala
            20                  25
```

<210> SEQ ID NO 7
<211> LENGTH: 27
<212> TYPE: PRT
<213> ORGANISM: Artificial Sequence
<220> FEATURE:
<223> OTHER INFORMATION: synthetic peptide

<400> SEQUENCE: 7

```
Ala Leu Trp Met Thr Leu Lys Lys Lys Val Leu Lys Ala Ala Ala Lys
1               5                   10                  15

Ala Leu Asn Ala Val Leu Val Gly Ala Asn Ala
            20                  25
```

<210> SEQ ID NO 8
<211> LENGTH: 27
<212> TYPE: PRT
<213> ORGANISM: Artificial Sequence
<220> FEATURE:
<223> OTHER INFORMATION: synthetic peptide

<400> SEQUENCE: 8

```
Ala Leu Trp Met Thr Leu Leu Lys Lys Val Leu Lys Ala Lys Ala Lys
1               5                   10                  15

Ala Leu Asn Ala Val Leu Val Gly Ala Asn Ala
            20                  25
```

<210> SEQ ID NO 9
<211> LENGTH: 27
<212> TYPE: PRT
<213> ORGANISM: Artificial Sequence
<220> FEATURE:
<223> OTHER INFORMATION: synthetic peptide

<400> SEQUENCE: 9

```
Ala Leu Trp Met Thr Leu Lys Lys Lys Val Leu Lys Ala Lys Ala Lys
1               5                   10                  15
```

```
1               5                   10                  15
Ala Leu Asn Ala Val Leu Val Gly Ala Asn Ala
            20                  25

<210> SEQ ID NO 10
<211> LENGTH: 18
<212> TYPE: PRT
<213> ORGANISM: Artificial Sequence
<220> FEATURE:
<223> OTHER INFORMATION: synthetic peptide

<400> SEQUENCE: 10

Glu Leu Glu Lys Gly Gly Leu Glu Gly Glu Lys Gly Gly Lys Glu Leu
1               5                   10                  15

Glu Lys

<210> SEQ ID NO 11
<211> LENGTH: 28
<212> TYPE: PRT
<213> ORGANISM: Artificial Sequence
<220> FEATURE:
<223> OTHER INFORMATION: synthetic peptide

<400> SEQUENCE: 11

Ala Leu Trp Met Thr Leu Leu Lys Lys Val Leu Lys Ala Ala Ala Lys
1               5                   10                  15

Ala Ala Leu Asn Ala Val Leu Val Gly Ala Asn Ala
            20                  25

<210> SEQ ID NO 12
<211> LENGTH: 28
<212> TYPE: PRT
<213> ORGANISM: Artificial Sequence
<220> FEATURE:
<223> OTHER INFORMATION: synthetic peptide

<400> SEQUENCE: 12

Ala Leu Trp Met Thr Leu Lys Lys Lys Val Leu Lys Ala Lys Ala Lys
1               5                   10                  15

Ala Ala Leu Asn Ala Val Leu Val Gly Ala Asn Ala
            20                  25

<210> SEQ ID NO 13
<211> LENGTH: 16
<212> TYPE: PRT
<213> ORGANISM: Artificial Sequence
<220> FEATURE:
<223> OTHER INFORMATION: synthetic peptide

<400> SEQUENCE: 13

Ala Leu Trp Met Thr Leu Lys Lys Lys Val Leu Lys Ala Lys Ala Lys
1               5                   10                  15

<210> SEQ ID NO 14
<211> LENGTH: 27
<212> TYPE: PRT
<213> ORGANISM: Artificial Sequence
<220> FEATURE:
<223> OTHER INFORMATION: synthetic peptide

<400> SEQUENCE: 14

Ala Leu Trp Met Thr Lys Leu Lys Lys Val Leu Lys Ala Lys Ala Lys
1               5                   10                  15

Ala Leu Asn Ala Val Leu Val Gly Ala Asn Ala
```

20                  25

<210> SEQ ID NO 15
<211> LENGTH: 27
<212> TYPE: PRT
<213> ORGANISM: Artificial Sequence
<220> FEATURE:
<223> OTHER INFORMATION: synthetic peptide

<400> SEQUENCE: 15

Ala Leu Trp Met Thr Leu Lys Lys Lys Val Leu Lys Ala Lys Ala Lys
1               5                   10                  15

Ala Leu Asn Ala Val Leu Ser Gly Ala Asn Ala
            20                  25

<210> SEQ ID NO 16
<211> LENGTH: 27
<212> TYPE: PRT
<213> ORGANISM: Artificial Sequence
<220> FEATURE:
<223> OTHER INFORMATION: synthetic peptide

<400> SEQUENCE: 16

Ala Leu Trp Met Thr Leu Lys Lys Lys Val Leu Lys Ala Lys Ala Lys
1               5                   10                  15

Ala Leu Asn Ala Val Leu Lys Gly Ala Asn Ala
            20                  25

<210> SEQ ID NO 17
<211> LENGTH: 27
<212> TYPE: PRT
<213> ORGANISM: Artificial Sequence
<220> FEATURE:
<223> OTHER INFORMATION: synthetic peptide

<400> SEQUENCE: 17

Ala Leu Trp Met Thr Leu Lys Lys Lys Val Leu Lys Ala Lys Ala Lys
1               5                   10                  15

Ala Leu Asn Ala Val Leu Ala Gly Val Asn Ala
            20                  25

<210> SEQ ID NO 18
<211> LENGTH: 27
<212> TYPE: PRT
<213> ORGANISM: Artificial Sequence
<220> FEATURE:
<223> OTHER INFORMATION: synthetic peptide

<400> SEQUENCE: 18

Ala Leu Trp Met Thr Leu Lys Lys Lys Val Leu Lys Ala Lys Ala Lys
1               5                   10                  15

Leu Leu Asn Ala Val Leu Val Gly Ala Asn Ala
            20                  25

<210> SEQ ID NO 19
<211> LENGTH: 27
<212> TYPE: PRT
<213> ORGANISM: Artificial Sequence
<220> FEATURE:
<223> OTHER INFORMATION: synthetic peptide

<400> SEQUENCE: 19

Ala Leu Trp Met Thr Leu Lys Lys Lys Val Leu Lys Ala Lys Ala Lys
1               5                   10                  15

```
Ala Leu Asn Ala Val Leu Val Gly Leu Asn Ala
            20                  25

<210> SEQ ID NO 20
<211> LENGTH: 27
<212> TYPE: PRT
<213> ORGANISM: Artificial Sequence
<220> FEATURE:
<223> OTHER INFORMATION: synthetic peptide

<400> SEQUENCE: 20

Ala Leu Trp Met Thr Leu Lys Lys Lys Val Leu Lys Ala Lys Ala Lys
1               5                   10                  15

Leu Leu Asn Ala Val Leu Val Gly Leu Asn Ala
            20                  25
```